US012295748B2

(12) United States Patent
Voigt et al.

(10) Patent No.: US 12,295,748 B2
(45) Date of Patent: May 13, 2025

(54) WEARABLE RING-TYPE SENSOR DEVICES FOR MONITORING HEALTH AND WELLNESS CONDITIONS

(71) Applicant: HHID, LLC, Pittsburgh, PA (US)

(72) Inventors: Thomas Voigt, Pittsburgh, PA (US); Swagatika Bhattacharya, Pittsburgh, PA (US)

(73) Assignee: HHID, LLC, Pittsburgh, PA (US)

( * ) Notice: Subject to any disclaimer, the term of this patent is extended or adjusted under 35 U.S.C. 154(b) by 0 days.

(21) Appl. No.: 18/080,644

(22) Filed: Dec. 13, 2022

(65) Prior Publication Data

US 2023/0181112 A1  Jun. 15, 2023

Related U.S. Application Data

(60) Provisional application No. 63/288,723, filed on Dec. 13, 2021.

(51) Int. Cl.
*A61B 5/00* (2006.01)
*A61B 5/0205* (2006.01)
(Continued)

(52) U.S. Cl.
CPC ............ *A61B 5/6826* (2013.01); *A61B 5/002* (2013.01); *A61B 5/02055* (2013.01);
(Continued)

(58) Field of Classification Search
None
See application file for complete search history.

(56) References Cited

U.S. PATENT DOCUMENTS 3,132,258 A  *  5/1964  Gaertner ................... H03F 7/04
                                                        330/4.9
6,289,238 B1 *  9/2001  Besson ............... H03F 3/45103
                                                        600/509
(Continued)

FOREIGN PATENT DOCUMENTS

WO    2021151154 A1    8/2021

OTHER PUBLICATIONS

International Search Report and Written Opinion for PCT Patent Application No. PCT/US22/81474 dated Mar. 17, 2023.

*Primary Examiner* — Carl H Layno
*Assistant Examiner* — Manolis Pahakis
(74) *Attorney, Agent, or Firm* — Michael D. Lazzara; Leech Tishman Fuscaldo & Lampl, LLC

(57) ABSTRACT

A ring-type wearable device is provided for sensing biometric data associated with various physiological conditions of the user. In one embodiment, a ring apparatus comprises a ring body including an opening formed therethrough structured to receive a body portion of a user therein when worn by the user; and an electronic computer processor programmed for processing one or more signals detected by the apparatus and associated with one or more biometrics associated with a physiological condition of the user into processed data. A light sensor system connected to the ring body includes multiple light-emitting diodes (LEDs), wherein each LED is associated with a predetermined light wavelength range, a first photodetector configured for light detection in a reflection mode, and a second photodetector configured for light detection in a transmission mode, each for detecting at least a portion of the light originating from the multiple LEDs.

26 Claims, 37 Drawing Sheets

(51) Int. Cl.
  *A61B 5/024* (2006.01)
  *A61B 5/11* (2006.01)
  *A61B 5/145* (2006.01)
  *A61B 5/1455* (2006.01)
  *A61B 5/332* (2021.01)
  *G01N 21/31* (2006.01)
  *G16H 40/67* (2018.01)

(52) U.S. Cl.
  CPC ...... *A61B 5/02416* (2013.01); *A61B 5/14552* (2013.01); *A61B 5/332* (2021.01); *A61B 5/4812* (2013.01); *A61B 5/4818* (2013.01); *A61B 5/4842* (2013.01); *G16H 40/67* (2018.01); *A61B 5/1112* (2013.01); *A61B 5/14532* (2013.01); *A61B 5/7455* (2013.01); *A61B 2560/0252* (2013.01); *A61B 2562/0219* (2013.01); *A61B 2562/0271* (2013.01); *G01N 2021/3181* (2013.01)

(56) References Cited

U.S. PATENT DOCUMENTS

| | | | |
|---|---|---|---|
| 10,219,709 B2* | 3/2019 | Basu | A61B 5/14552 |
| 10,568,525 B1* | 2/2020 | Wu | A61B 5/6824 |
| 10,709,339 B1* | 7/2020 | Lusted | A61B 5/282 |
| 10,777,314 B1* | 9/2020 | Williams | A61B 5/4866 |
| 10,918,289 B1* | 2/2021 | Wasson | G01N 21/3151 |
| 11,154,231 B2* | 10/2021 | Coleman | A61B 5/318 |
| 11,324,292 B2* | 5/2022 | Min | A61B 5/0006 |
| 11,330,993 B2* | 5/2022 | Basu | A61B 5/1455 |
| 2009/0203972 A1* | 8/2009 | Heneghan | G16H 40/63 600/301 |
| 2010/0081942 A1* | 4/2010 | Huiku | G16H 40/60 600/483 |
| 2011/0251985 A1* | 10/2011 | Waxman | G16H 10/60 706/20 |
| 2014/0139486 A1* | 5/2014 | Mistry | G06F 3/011 345/175 |
| 2015/0141774 A1* | 5/2015 | Ogawa | A61B 5/0205 600/521 |
| 2015/0157269 A1* | 6/2015 | Lisogurski | A61B 5/0295 600/301 |
| 2015/0220109 A1* | 8/2015 | von Badinski | H02S 40/22 368/10 |
| 2015/0320588 A1* | 11/2015 | Connor | F24F 11/0001 607/104 |
| 2016/0139273 A1* | 5/2016 | Sobol | G01S 19/14 342/357.52 |
| 2017/0014035 A1* | 1/2017 | Newberry | A61B 90/96 |
| 2017/0020399 A1* | 1/2017 | Shemesh | A61B 5/02416 |
| 2017/0215811 A1* | 8/2017 | Newberry | A61B 5/14532 |
| 2017/0258336 A1* | 9/2017 | Furness, III | A61B 5/026 |
| 2017/0372026 A1* | 12/2017 | Sanyal | A61B 5/681 |
| 2018/0020937 A1* | 1/2018 | Chou | A61B 5/291 600/301 |
| 2018/0110450 A1* | 4/2018 | Lamego | A61B 5/0022 |
| 2018/0132789 A1* | 5/2018 | Chen | A61B 5/02438 |
| 2018/0146870 A1* | 5/2018 | Shemesh | A61B 5/02416 |
| 2018/0253151 A1* | 9/2018 | Kletsov | A61B 5/004 |
| 2020/0004415 A1* | 1/2020 | Warren | G06F 3/162 |
| 2020/0139112 A1* | 5/2020 | Aharonovitch | A61B 5/4812 |
| 2020/0194905 A1* | 6/2020 | Wei | A61B 5/0006 |
| 2020/0237303 A1* | 7/2020 | Ferber | A61B 5/02416 |
| 2020/0237317 A1* | 7/2020 | Newberry | A61B 5/1455 |
| 2020/0342086 A1* | 10/2020 | Oung | H04L 63/0861 |
| 2020/0383628 A1* | 12/2020 | Borremans | A61B 5/02427 |
| 2021/0022676 A1* | 1/2021 | Lamego | A61B 5/02055 |
| 2021/0037932 A1* | 2/2021 | Min | A61B 5/0006 |
| 2021/0074421 A1* | 3/2021 | Gopalakrishnan | A61B 5/02055 |
| 2021/0169345 A1* | 6/2021 | Wasson | A61B 5/14546 |
| 2021/0177353 A1* | 6/2021 | Bhagat | A61B 5/02055 |
| 2021/0278561 A1* | 9/2021 | Mehra | A61B 5/681 |
| 2021/0393154 A1* | 12/2021 | Gelissen | A61B 5/02427 |
| 2022/0233119 A1* | 7/2022 | Shelton, IV | A61B 17/07207 |
| 2022/0399123 A1* | 12/2022 | Nichols | G16H 30/40 |
| 2023/0043018 A1* | 2/2023 | Wai | H01Q 9/265 |
| 2024/0315646 A1* | 9/2024 | Maderic | A61B 5/681 |

\* cited by examiner

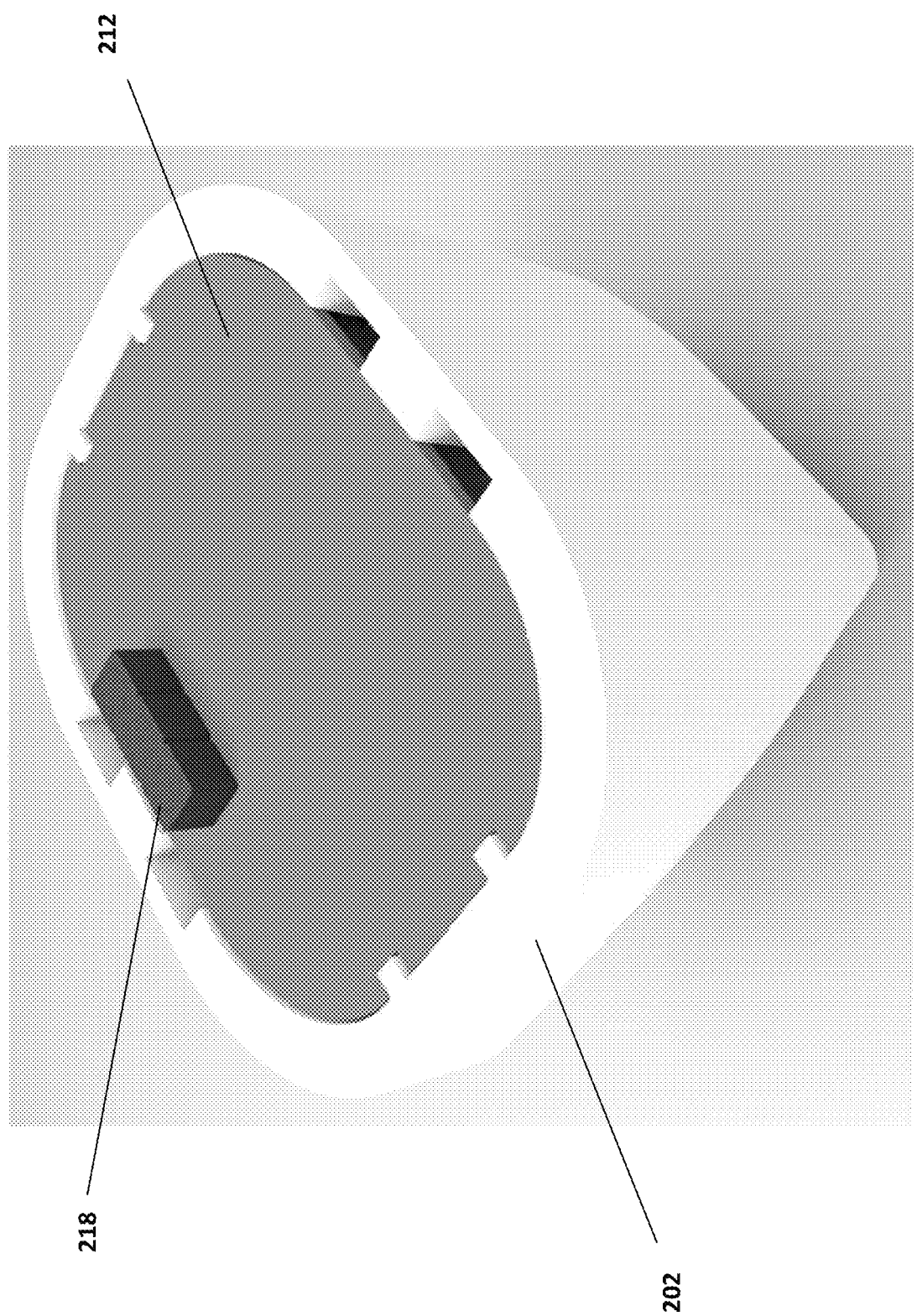

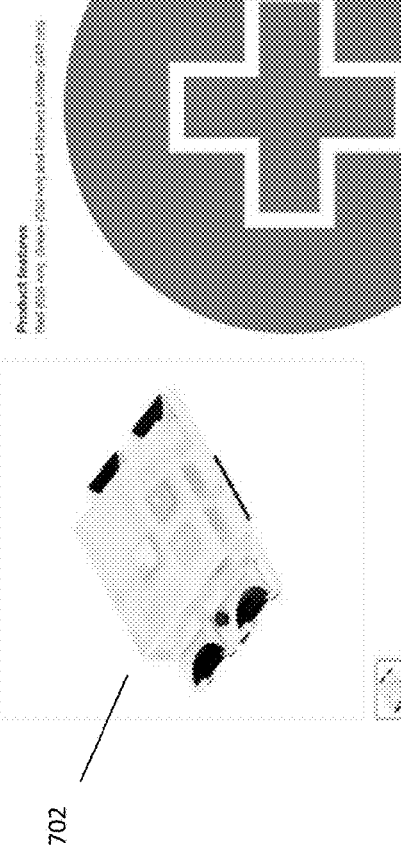
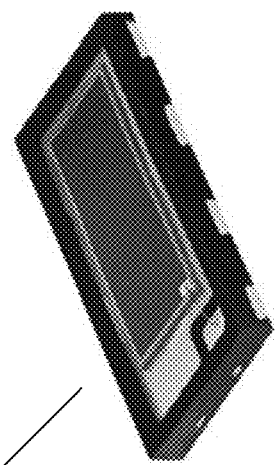
FIG. 7C

15 Key Biometrics of Wearable Sensor Ring

- Blood oxygen (SpO2) *
- Blood pressure *
- Heart rate
- Heart rate variability (HRV)
- Resting heart rate
- Respiratory rate
- Temperature on skin
- Activity detection
- Temperature of environment
- Steps
- Accelerometer
- Calories burned
- Electrocardiogram (ECG) *
- Sleep stages
- Sleep apnea detection

My Metrics / Share My Data Wireframes

*My Metrics (continued)*

*My Metrics (continued)*

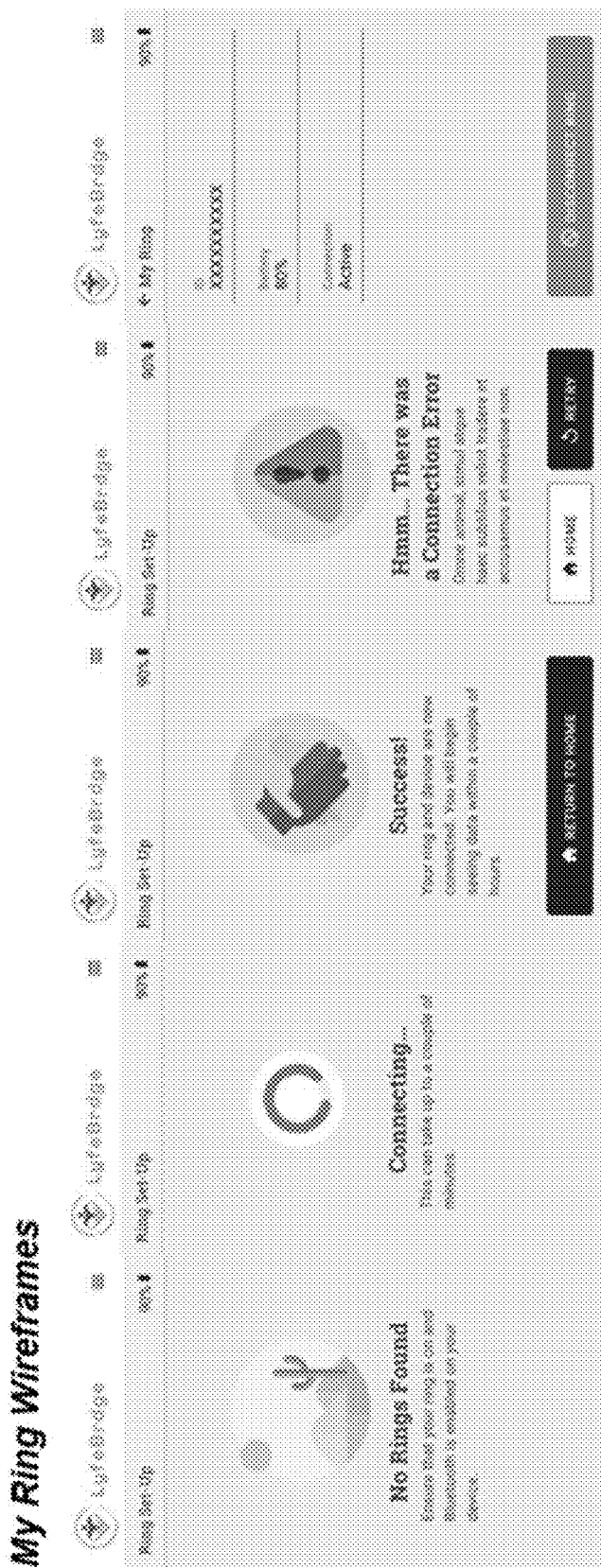

Login Wireframes (continued)

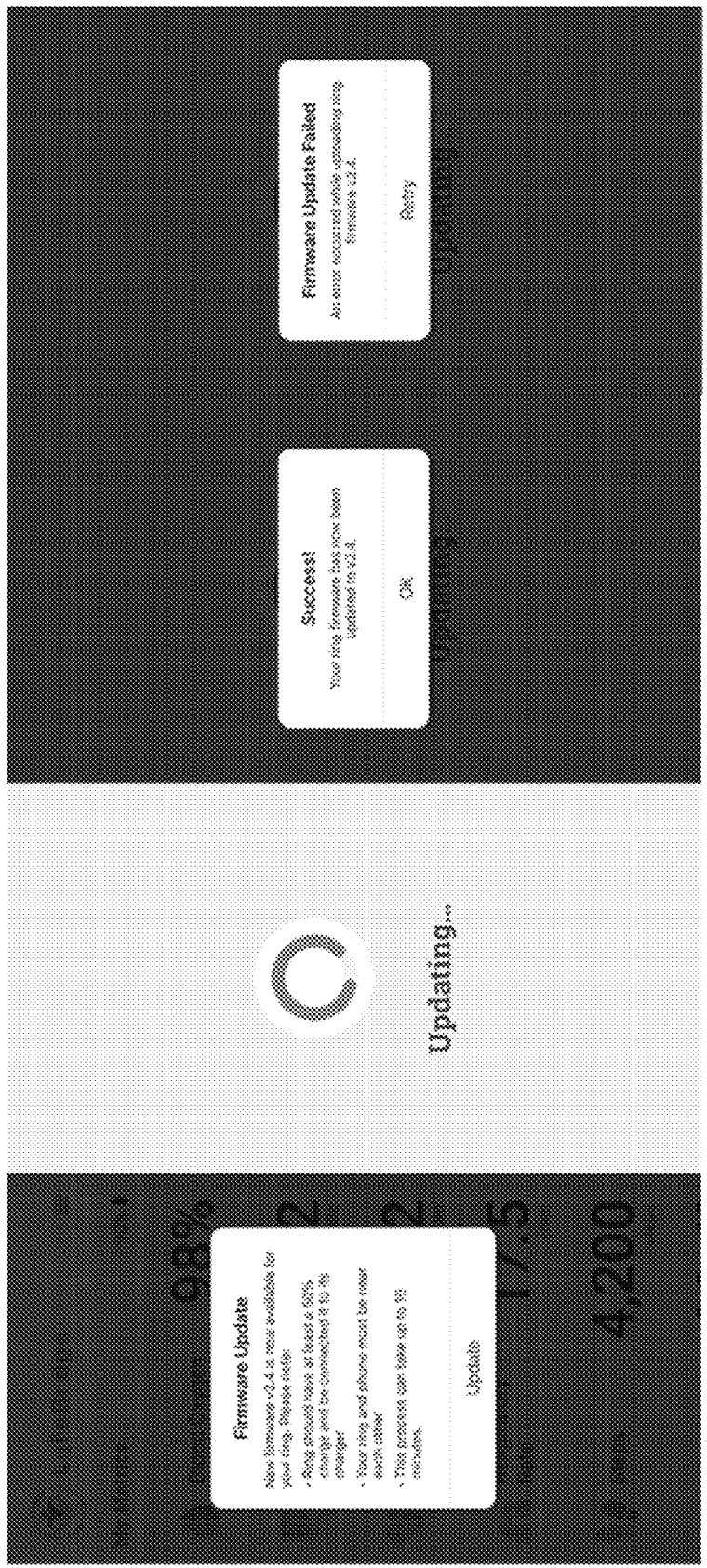

FIG. 48 ered to communicate data sensed and collected by action of

WEARABLE RING-TYPE SENSOR DEVICES FOR MONITORING HEALTH AND WELLNESS CONDITIONS

CROSS-REFERENCE TO RELATED APPLICATION/PRIORITY CLAIM

The present application claims the priority benefit of U.S. Provisional patent Application Ser. No. 63/288,723, filed on Dec. 13, 2021, the entirety of which is hereby incorporated by reference into the present application.

FIELD OF THE INVENTION

Various embodiments of the present invention generally relate to devices, systems, processes, and techniques for monitoring health and wellness conditions of a user by means of a wearable device. In particular embodiments, the wearable device may comprise a ring-type wearable device suitable to be worn by a user for sensing biometric data associated with various physiological conditions of the user.

BACKGROUND

Wearable electronic devices can operate in a variety of ways to assist their users with promoting health and fitness. FIG. 1 illustrates various examples of different types of devices, such as watches, bracelets, and eyeglasses, which can be worn in alternative ways to monitor and collect data associated with physiological conditions of their users. However, in many situations, a fundamental level of suitable physical fitness is assumed for the user wearing the device (e.g., a physically fit and healthy runner training to run a marathon). Conventional devices ignore the fact that many kinds of users are advanced in age, suffer from physical ailments, disabilities, or who have intellectual disabilities or other challenges which significantly limit their ability to take full advantage of the benefits of such devices.

Therefore, enhanced tools and techniques are needed that provide wearable sensor devices to monitor key health metrics for a wider variety of different users. For example, caring for long-term and home care patients depends on complete and accurate data. Physiological conditions of these patients, such as body temperature, heart rate, blood pressure, blood oxygen saturation (SpO2), and other conditions should be measured, monitored, and charted multiple times per day. Medical care professionals in a 100-bed facility, for example, may need to spend significant time collecting and charting patient data to improve patient care. Accordingly, computer-based tools are needed for automating this process to establish baseline data and chart exceptional events more accurately while reducing opportunities for manual transcription errors.

BRIEF DESCRIPTION OF THE FIGURES

FIG. 5 is a three-dimensional view of the ring of FIG. 2A with a top portion removed to illustrate various internal components of the ring.

FIG. 7C illustrates examples of LED and photodetector components which can be employed by different ring devices.

FIG. 9A depicts an overview summary of different examples of the kinds of biometric measurement data which can be sensed, collected, and then analyzed data in connection with use of a ring.

FIGS. 9B and 9C include a table illustrating examples of different biometric data which can be collected by use of a ring device.

FIGS. 17 through 32 include various wireframe representations of examples of user interface screens which can be generated and displayed on a user access device in connection with a ring device.

FIGS. 33 through 37 include various wireframe representations of examples of user interface screens which can be generated and displayed on a user access device to show information for a ring device.

Figures 38, 39, 40, 41:
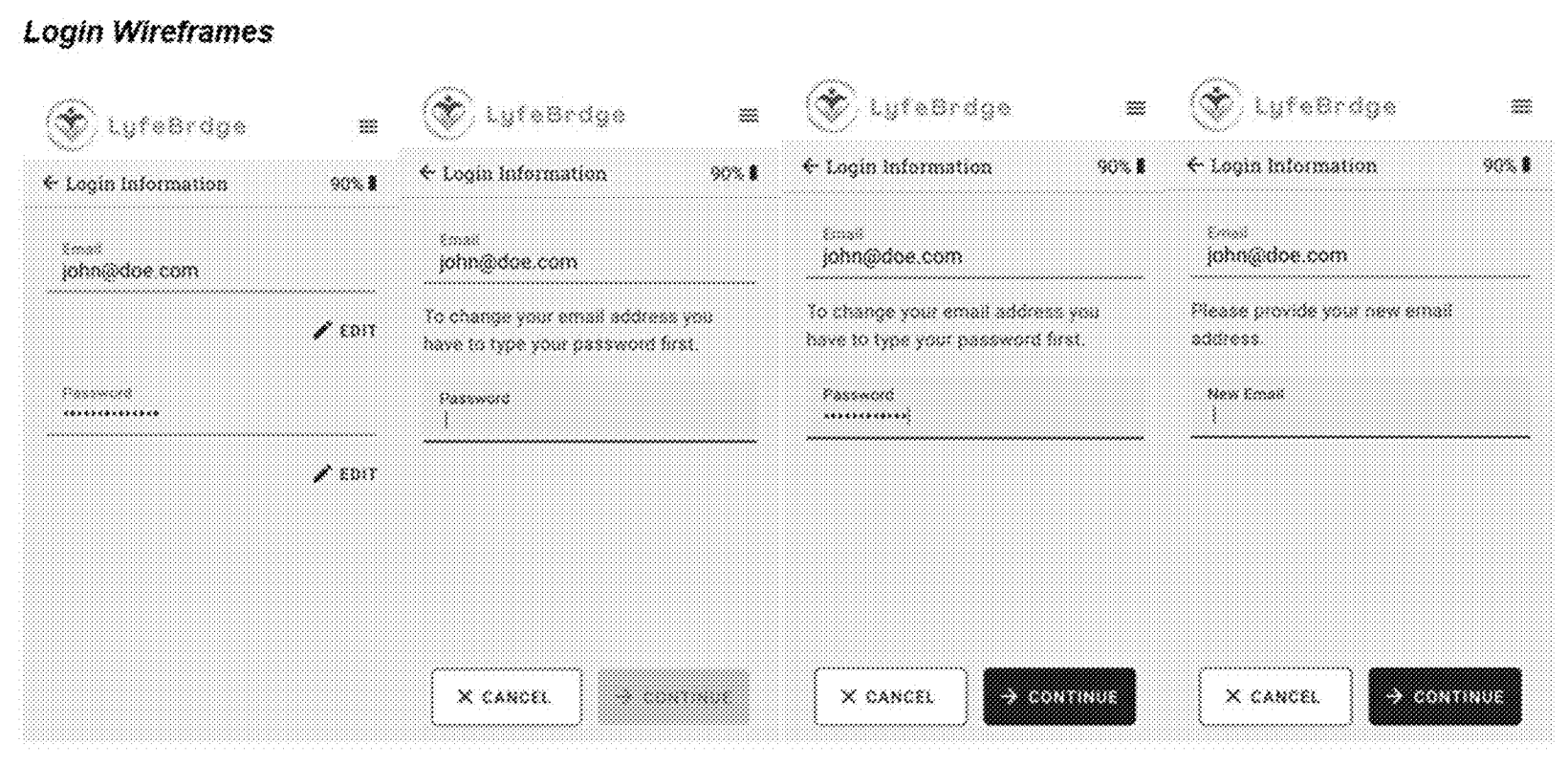
Figures 42, 43:
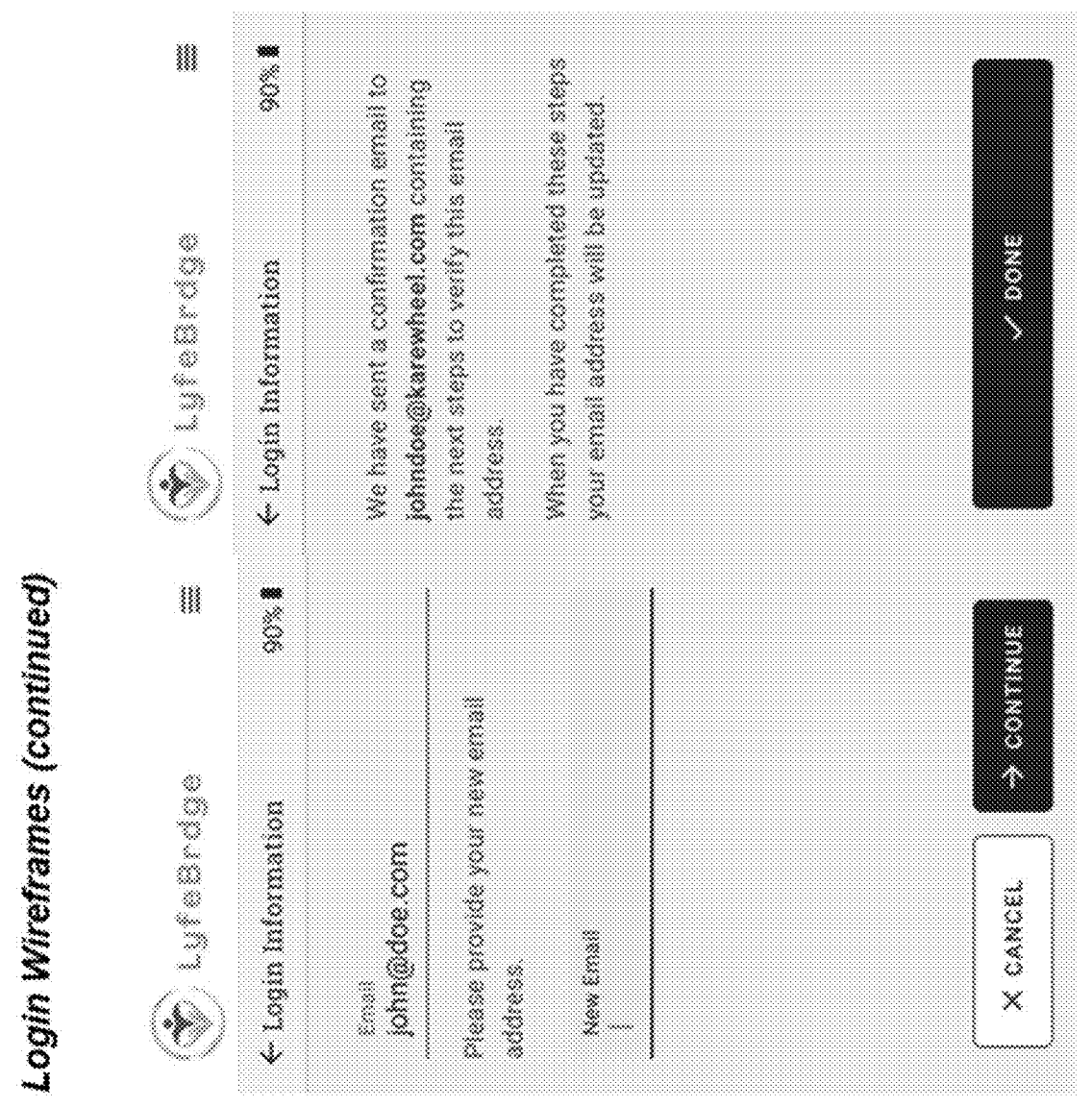

FIGS. 38 through 43 include various wireframe representations of examples of user interface screens which can be generated and displayed on a user access device to show user login information and procedures for a ring device.

FIGS. 44 through 47 include various wireframe representations of examples of user interface screens which can be generated and displayed on a user access device to show firmware updates for a ring device.

Figure 48:
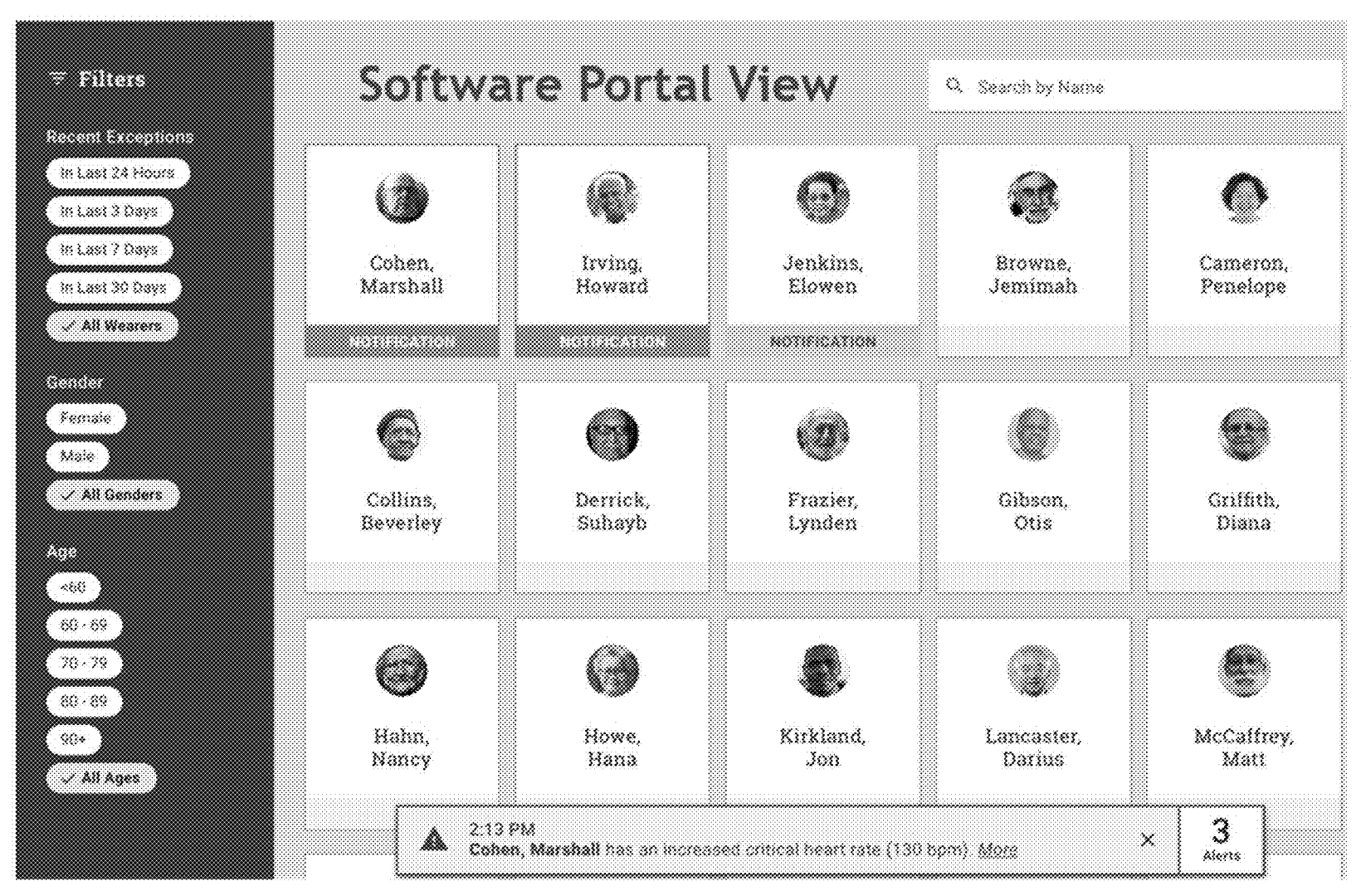

FIG. 48 illustrates an example of a facility portal view for data obtained from multiple ring devices associated with a patient population.

DESCRIPTION

Figure 1:
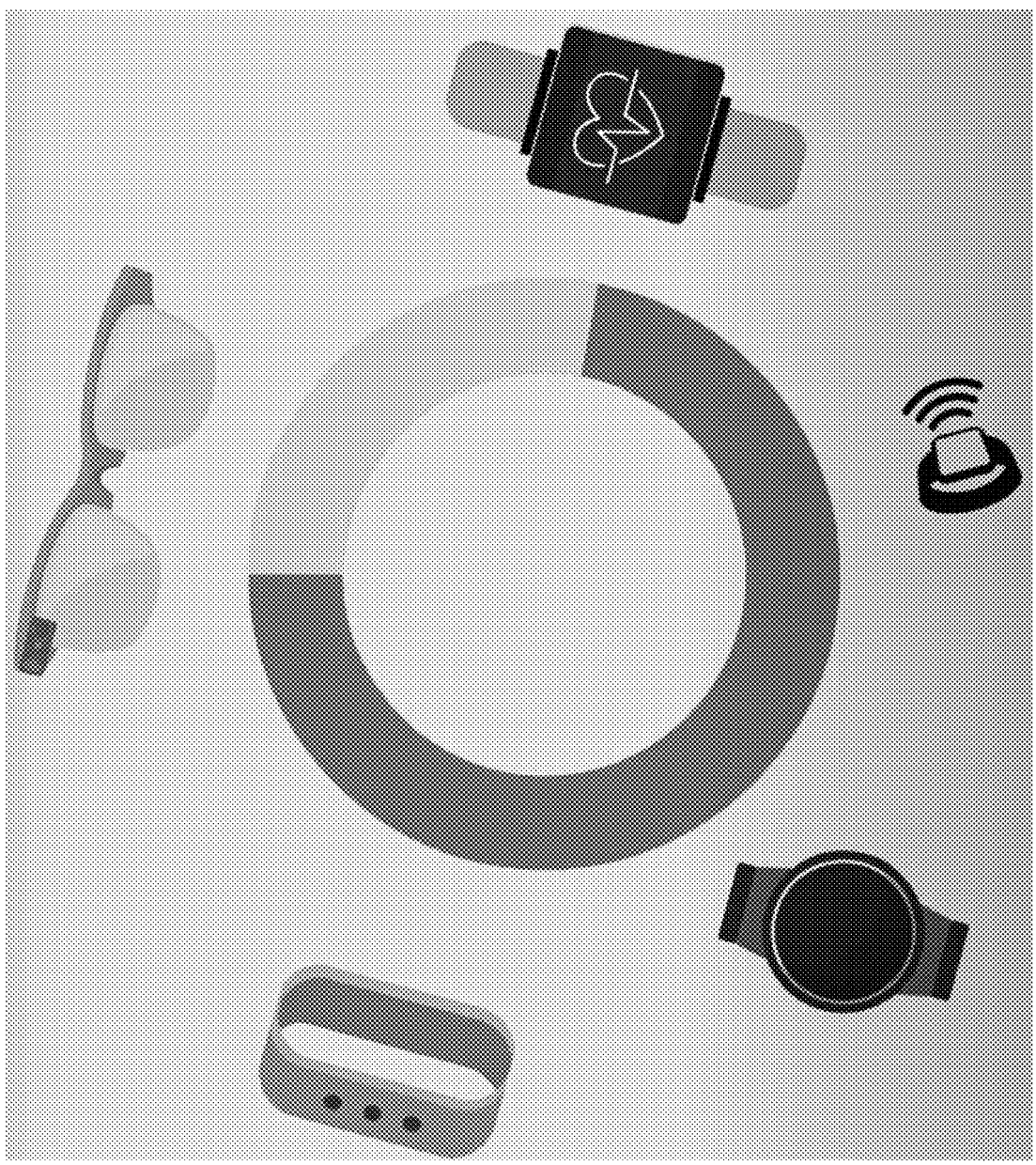
FIG. 1 (prior art) illustrates various examples of different types of devices which can be worn in alternative ways to monitor and collect data associated with physiological conditions of their users.

In various embodiments described herein, a wearable, ring-type device can be structured and programmed for improving the health and wellness of users, including users with intellectual and/or physical disabilities who cannot use or cannot fully benefit from other types of wearable devices (e.g., watches, bracelets, or eyeglasses). In certain embodiments, Internet-of-Things (IoT) technology can be incorporated into ring-type wearable devices equipped with sensors to facilitate collecting and processing physiological data, environmental data, and key health metric data, among other condition data associated with a user. In certain embodiments, such collected and processed data can be used for creating and presenting intelligent dashboards on user interface screens. These smart dashboards can leverage data analytics and machine learning tools, for example, to create a holistic picture of individual health performance. The wearable device can be programmed for automatic, continuous, and real-time measurements of health performance that can be used to minimize individual health risks and enable a healthy lifestyle. In certain embodiments, the device can be structured and/or programmed to focus on users to promote their care management, disease management, physical therapy and rehabilitation, among other health-oriented activities. In one aspect, the wearable device can also enable anomaly notification for the user through an operatively associated vibration tool, for example, positioned in the ring-type device, as well as notification-type communications with health professionals which relay information about the user's current condition.

An apparatus can be provided which comprises: a ring body including an opening formed therethrough structured to receive a body portion of a user therein when worn by the user; a power source positioned within the ring body and configured for supplying power to at least one other component of the apparatus; an electronic computer processor programmed for: processing one or more signals detected by the apparatus and associated with one or more biometrics associated with a physiological condition of the user into processed data, and storing at least a portion of the unprocessed data and/or the processed data associated with the detected biometric signals; and a light sensor system connected to the ring body. The light sensor system can include multiple light-emitting diodes (LEDs), wherein each LED is associated with a predetermined light wavelength range, a first photodetector configured for light detection in a reflection mode for detecting at least a portion of the light originating from the multiple LEDs and transmitted to the first photodetector, at least a second photodetector configured for light detection in a transmission mode for detecting at least a portion of the light originating from the multiple LEDs and transmitted to the first photodetector, and the light sensor system can be programmed for communicating signals indicative of light detected by the photodetectors to the processor.

In certain embodiments, the apparatus can include an electrocardiogram (ECG) sensor system comprising multiple metal contacts configured for communicating signals indicative of at least one cardiological condition of the user when the metal contacts are in contact with at least a portion of skin of the user. One of the multiple metal contacts is a finger contact accessible by a finger of the user for initiating an ECG measurement for the user when the apparatus is worn by the user. The apparatus can include a vibrator positioned within the ring body which is programmed for vibrating in response to receiving an anomaly notification signal from the processor (e.g., the anomaly notification can be generated and communicated from an external computer system).

In other aspects, the apparatus can include an accelerometer positioned within the ring body which is programmed for detecting at least one change in movement of the ring body; and communicating a signal to the processor indicative of the detected change in movement. The processor can be programmed for receiving at least one signal from the accelerometer indicative of detecting a fall by the user or a sleep stage of the user (e.g., nap detection). The apparatus can include a global positioning system (GPS) module positioned in the ring body. In certain embodiments, the apparatus can include at least one temperature sensor operatively associated with the ring body. The temperature sensor may be configured to detect an ambient temperature in the environment around the ring body and/or to detect a temperature of the user.

In certain embodiments, an electrical charger can be configured for charging the power source, the charger being magnetically attachable and/or detachable from the ring body, and the charger configured for conveniently charging power source when the apparatus is in use. In other aspects, the apparatus can include a low energy Bluetooth (BLE) component positioned in the ring body which is configured for facilitating communicating at least a portion of the processed data and/or the unprocessed data from the ring body to a mobile access device; and an antenna operatively associated with the ring body for communicating at least a portion of the processed data and/or the unprocessed data to at least one external computer system via a wireless communication network.

The apparatus can include one or more different kinds of non-volatile data storage media configured for retaining at least a portion of the processed data or unprocessed data when the power supply is disrupted or drained. In various embodiments, the apparatus can have a ring body with at least a portion comprised of a resiliently flexible and/or elastic material. In one embodiment, at least a portion of the resiliently flexible and/or elastic material comprises a flexible electronic substrate, and at least one of the multiple LEDs embedded in the flexible electronic substrate for promoting contact of the embedded LED with at least a portion of skin of the user when the apparatus is in use. The ring body comprises a material that is at least one or more of scratch-resistant, hypoallergenic, and/or water resistant.

In various embodiments, the apparatus can include a data communication module positioned in the ring body which is programmed for communicating at least a portion of the unprocessed and/or processed data collected by the apparatus to at least one external computer system. The communicated data can be associated with signals collected by the light sensor system and is configured for determining a blood oxygen level of the user, for example. The external computer system can be programmed for determining at least one anomaly notification in response to at least a portion of the communicated data. At least a portion of the communicated data can include medical grade data. The data communication module can be programmed for communicating the processed data to an artificial intelligence module programmed for sleep apnea detection and/or blood glucose level detection. The data communication module can be programmed for communicating biometric data associated with one or more of blood oxygen level, blood pressure, heart rate, heart rate variability, resting heart rate, respiratory rate, skin temperature, ambient environment temperature, user activity detection, user steps taken, accelerometer data, sleep stage, and/or sleep apnea data. At least a portion of the communicated unprocessed data and/or processed data can be associated with data for generating a photoplethysmography (PPG) waveform in connection with determining a blood pressure of the user, for example.

In certain embodiments, the light sensor system of the apparatus can be programmed for communicating signals indicative of light detected by the photodetectors independent of a skin pigment of a user. The light sensor system can be programmed for communicating signals indicative of light detected by the photodetectors independent of a skin pigment of a user in response to a combination of a predetermined location of at least one of the multiple LEDs on the ring body, and a predetermined frequency of at least one of the multiple LEDs.

The light of the LEDs can be impacted and detected in intensity (e.g., absorption and/or reflection), and impacted and detected in the signal (pulse) form and/or the waveform (e.g., HR, PPG, and ECG). The wearable ring device can include a dual communication tool (BLE and WiFi through a customized antenna). The wearable ring works with application software to visualize processed medical data in a portal (e.g., a view for healthcare professionals of all patients wearing rings in an overview of their biometrics), including generating various types of anomaly notifications for biometric data outside of expected or predetermined value range. Medical grade data communicated from a cloud computing environment can be linked to a health care facility's API, for example, and from there into an electronic medical record (EMR) system for various patients. In other embodiments, the data communication module of the apparatus can be programmed for communicating biometric data useable by the external computer system for determining detection of early stage disease development.

FIGS. 2 through 6C depict various aspects of one example of a ring-type wearable device 202 structured in accordance with certain embodiments of the present invention. The device 202 may include an opening 204 extending therethrough, which can be suitably sized for receiving a finger or other digit of a user, for example. Portions of the ring 202 in contact with the body of the user can be comprised of a resiliently flexible or elastic material which allows for variations in ring sizes, for example, of different users, or perhaps variations or changes in ring size experienced by the same user (e.g., the ring size of the user may change due to temperature or other weather-related environment conditions). In one alternative embodiment, a super magnet band can be used as part of the portion of the ring 202 body which encases the finger of a user, for example. The ring 202 body material can be structured to be lightweight, scratch-resistant, hypoallergenic, or water resistant, among other characteristics driven by the user's environment, the user's physical condition, and/or user preferences.

In certain embodiments, a blood oxygen sensor or pulse oximeter sensor system may be incorporated into the body of the ring 202 near the opening 204. In this example, multiple LEDs 206, 208, 210, each of which may be associated with different wavelengths, operate in association with a photodetector 207 for light detection in a reflection mode and with a photodetector 209 for light detection in a transmission mode to collect and process data associated with detecting and measuring a user's blood oxygen level, for example. In combination, the LEDs 206, 208, 210, and the photodetectors 207, 209 may be considered a light sensor system for the device 202.

In various embodiments, the light sensor system can leverage a photoplethysmography (PPG) phenomenon associated with a user's cardiovascular system. As the user's heart pumps out blood with systolic pressure, arteries can change their diameter, and this results a high absorption rate of LED light transmitted to the arteries. Alternatively, as the user's heart pumps in blood with diastolic pressure, the arteries can change their diameter, and this results a high absorption rate of LED light transmitted to the arteries. For example, when the heart pumps blood inward, the diameter of the artery is reduced and there is less absorption of light due to a lower volume of blood flow. Generating a PPG waveform (the electronic signal of the pulse) reflects these two phases of transmittance and reflectance and can be used to detect heart rate (HR) and/or blood pressure.

In certain embodiments, multiple wavelength LEDs 206, 208, 210 can be used. In one example, one LED may be a green (e.g., in the 530 nm wavelength range), another LED may be red (e.g., in the 660 nm wavelength range, small bandwidth <30 nm), and another LED may be infrared (e.g., in the 940 nm wavelength). Multiple wavelengths can be used for reflection mode. For heart rate (HR) measurement, the relative change of the light absorption can be used. For blood oxygen saturation measurement (SpO2), absolute signal values can be used with medically certified LEDs (e.g., OSRAM) to promote obtaining medical grade data. For the SpO2 measurement, red and infrared LEDs can be used, inv view of the fact that absorption of light in the blood is changing relatively quickly in the red wavelength, therefore the small bandwidth LEDs can be used to obtain medical grade data. The pulse oximetry measurement involves analyzing the signal intensity ratio (Imin/Imax); the pulses are relatively short (<0.3 msec) and they repeat relatively rapidly (>2 msec). The LEDs can be configured to facilitate a continuous blood pressure observation.

Because the hemoglobin in the blood absorbs light, the change in the amount of blood in the arteries can be measured optically. The excitation wavelength penetrates tissue and blood vessels. The incident light is absorbed, transmitted or reflected to the photodetector (see FIG. 6E). An electrical signal is generated as a function of the degree of absorption in the tissue, in the veins, and in the arteries. The part of the blood volume in the arteries that pulsates with the heartbeat is responsible for the changing signal part. The pulse can therefore be determined from the periodicity of the photodetector signal. Depending on the part of the body, different wavelengths are suitable for these measurements. For example, red and infrared light can be used on the finger or in the ear.

With a light sensor system equipped with infrared and red light, the oxygen saturation of the arterial blood can also be calculated from the measurement data. Pulse oximetry can be used to determine blood oxygen saturation non-invasively with the ring device. The method can be based on the fact that oxygen-poor and oxygen-rich blood absorb light differently. The body's own molecule hemoglobin (Hb), which carries oxygen in the blood, is optically active. Hemoglobin changes its absorption behavior with the binding of oxygen (oxyhemoglobin HbO2), therefore it is sufficient for pulse oximetry just to touch the sensor with a finger.

A processor (CPU) 212 can be incorporated into the ring 202 having flex electronics on one or both sides of the processor 212. Such flex electronics can be used to house one or more of the LEDs 206, 208, 210, to promote contact of the finger skin of a ring wearer, for example, with the LEDs 206, 208, 210. The processor 212 can be programmed to receive, process, and store data collected from the various sensors and other devices included in the ring 202, and to direct tasks performed by different components of the ring 202. In other aspects, a vibrator 214 can be included in the ring 202, as well as an accelerometer or other device programmed to detect changes in movement by a user. The vibrator 214 can be used to inform the user of an anomaly notification, for example, as well as to generate and communicate with healthcare professionals to give notifications indicative of user movement changes. In certain embodiments, a global positioning system (GPS) module 216 can be installed in the ring 202, such as to facilitate determining or identifying a location of the user wearing the ring 202, for example, or to locate the ring 202 itself, such as in the event that the ring 202 itself (or its wearer) might become lost.

In various embodiments, temperature sensors 217, 218 can be employed to detect temperatures relevant to the user's personal condition and/or the user's ambient environment. Temperature sensor 217 can be structured for contact with the skin of the user and programmed to detect a temperature level of the user. Temperature sensor 218 can be programmed to detect a temperature of the ambient environment in which the ring 202 and/or the user are located. It can be appreciated that changes in temperature can be calculated to indicate a change in the user's personal body temperature condition or a change in the temperature of the user's ambient environment. Temperature changes can be further tracked and monitored for trend detection or forecasting purposes.

In certain embodiments, the ring 202 can be configured to generate an electrocardiogram (e.g., "ECG" or "EKG") associated with the heart rate, for example, of a wearer of the ring 202. The ring 202 can be programmed to detect anomalies in the heart rate to trigger an ECG or other anomaly notifications. In one aspect, the ring 202 many include a band with metal contacts for establishing contact with the skin of the finger of the wearer, for example. Also, a top portion of the ring 202 may include a separate metal contact, which allows the user to be in contact with both the ring 202 finger and another finger (e.g., a finger of the non-ring hand of the wearer) to thereby create an electrical circuit and initiate an ECG measurement for the wearer.

Figure 2A:
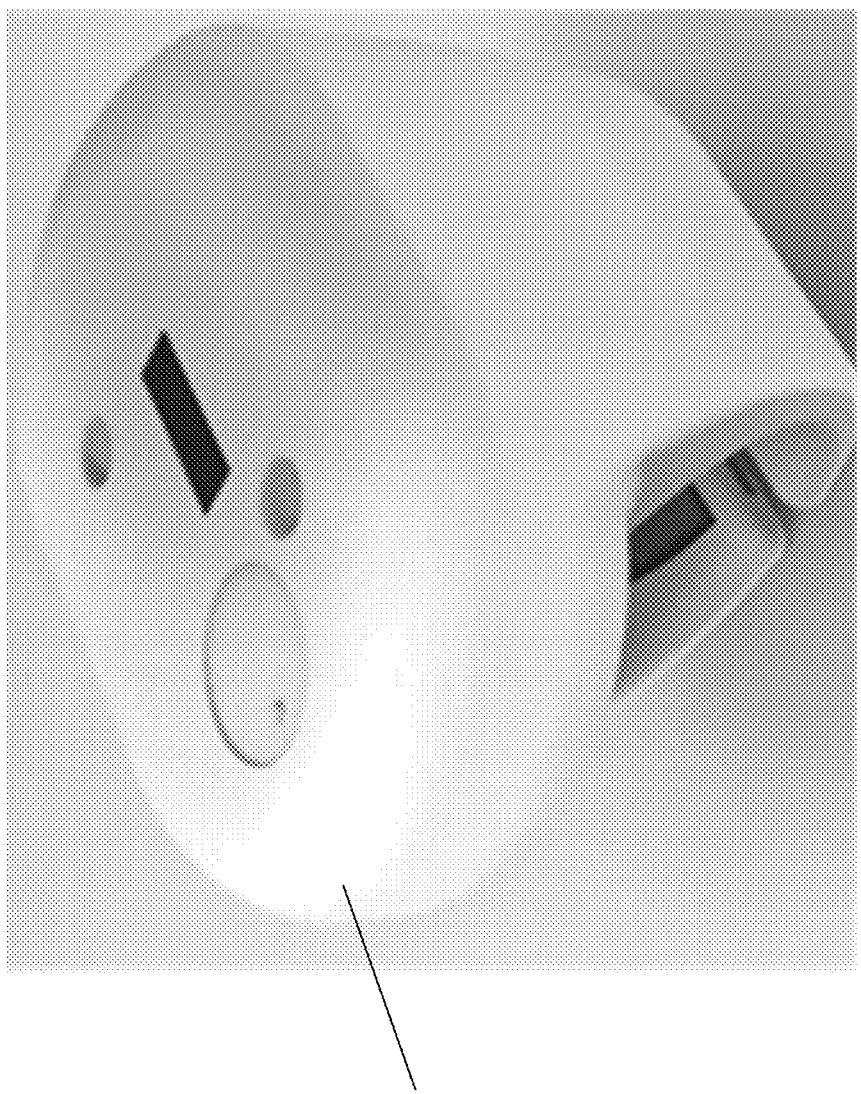
FIG. 2A is a three-dimensional view of one example of a ring-type wearable device.
Figure 2B:
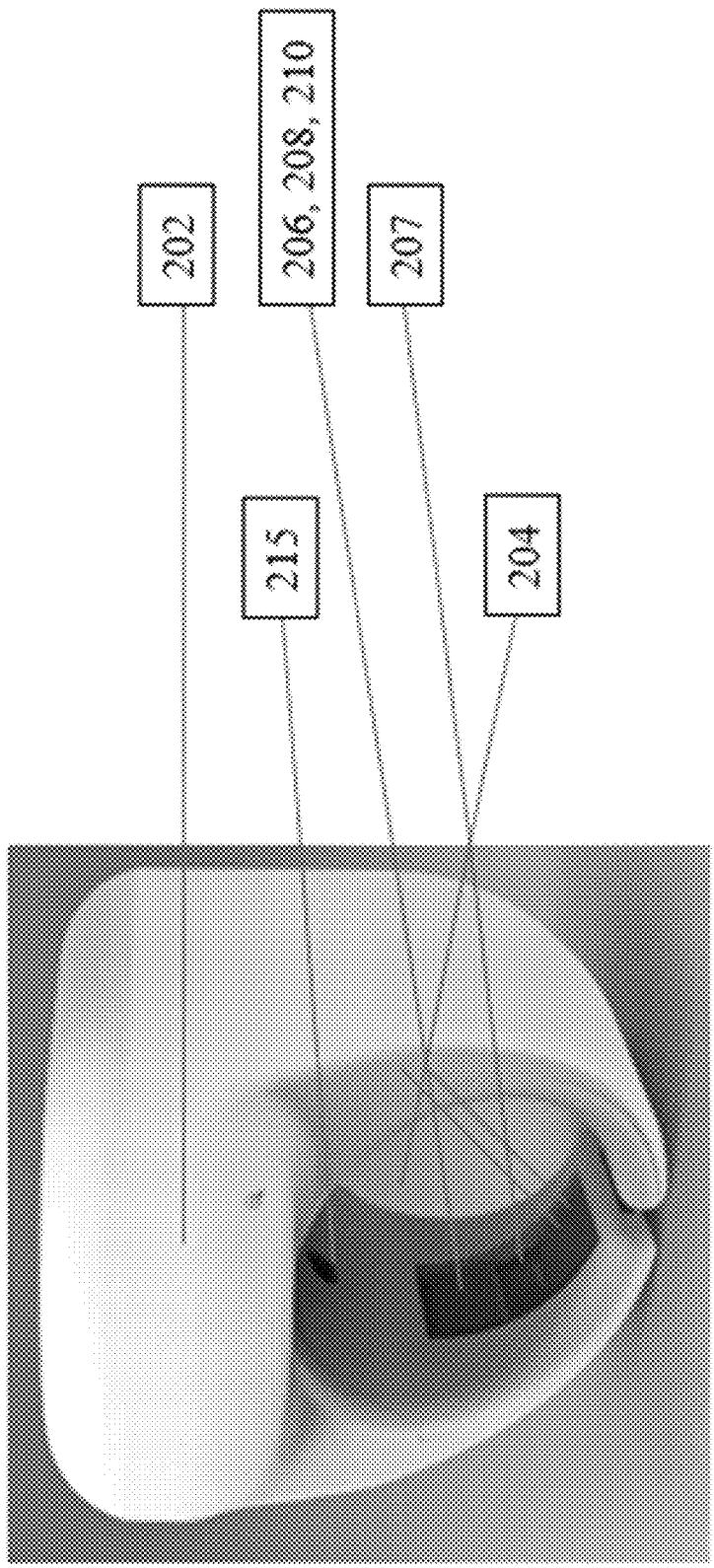
FIG. 2B is an alternative view of the ring device shown in FIG. 2A.
Figure 2C:
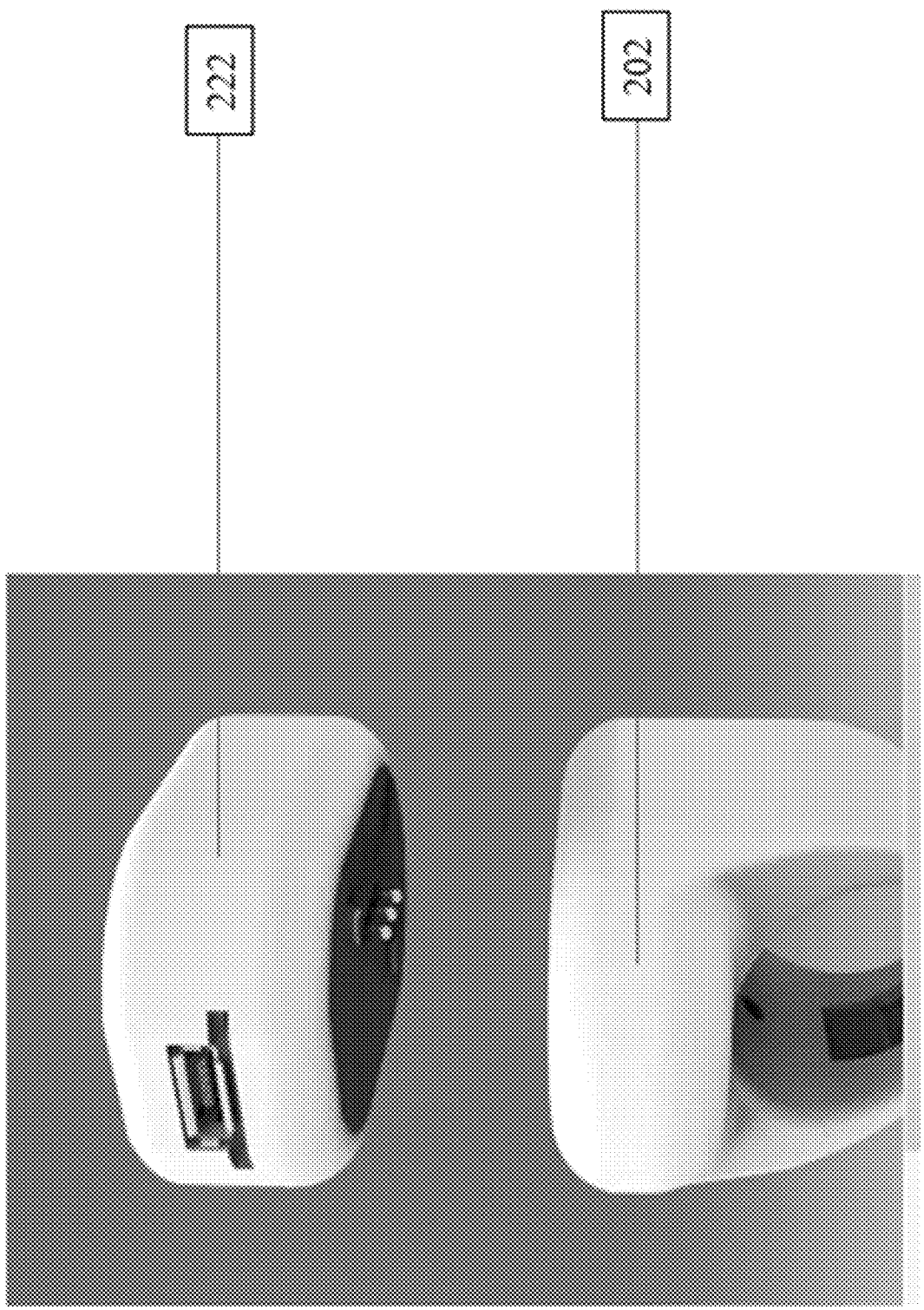
FIG. 2C illustrates an example of how a charger can be fixed on top of a ring through mechanical and magnetic tools and connected to a ring battery through a top portion of the ring.
Figure 3:
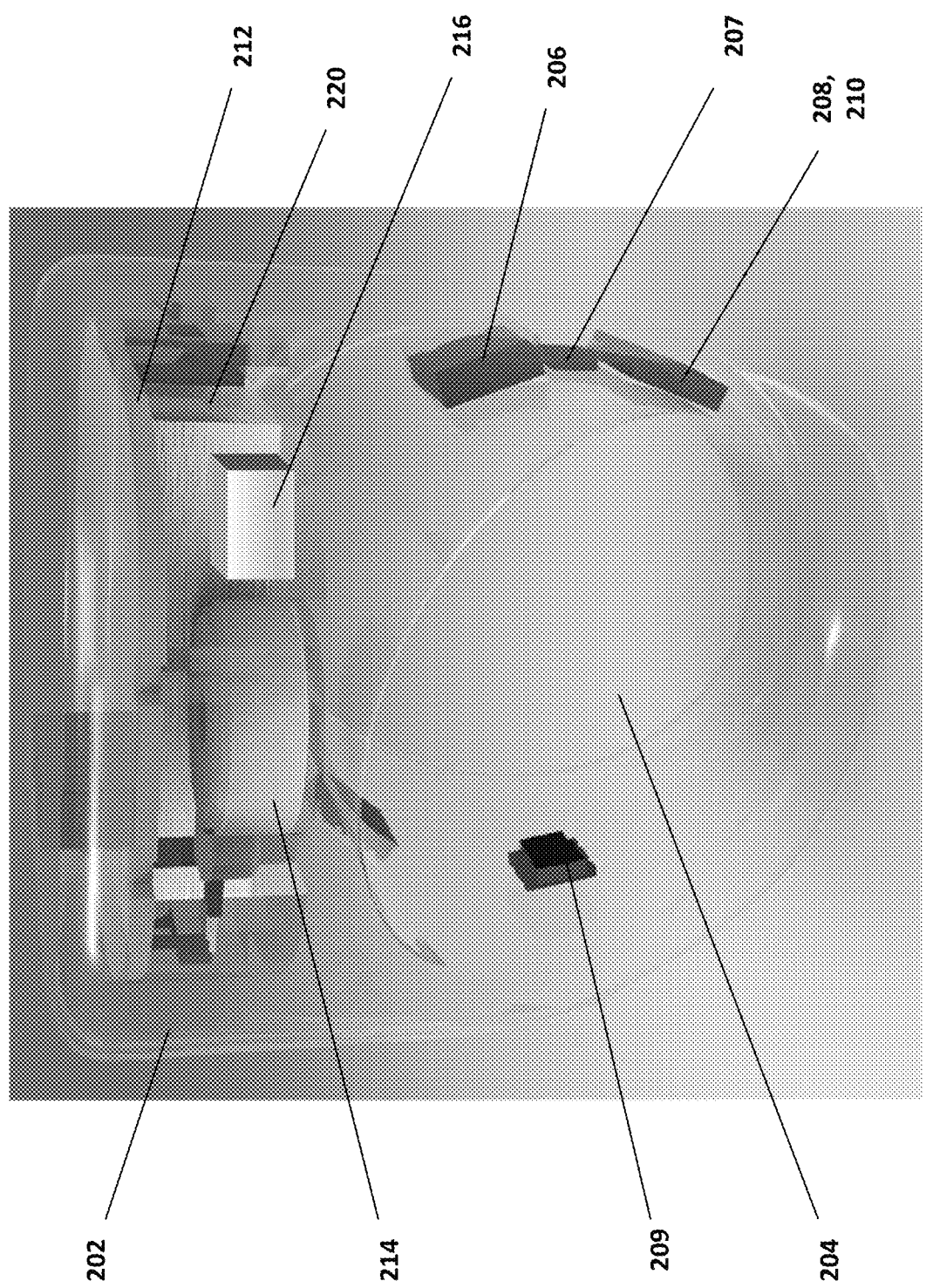
FIG. 3 is a transparent three-dimensional view of one example of a ring-type wearable device.
Figure 4:
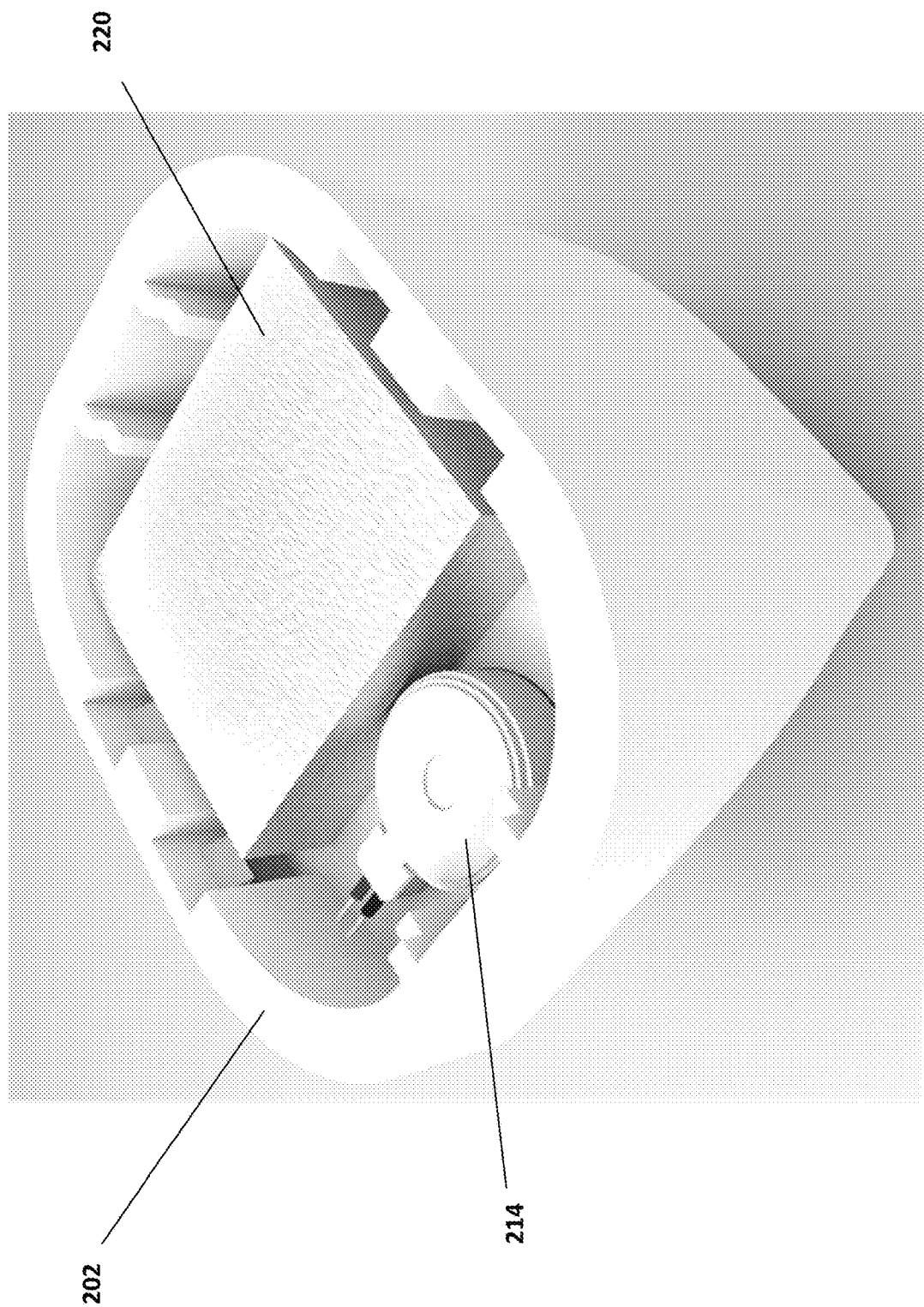
FIG. 4 is a three-dimensional view of the ring of FIG. 2A with a top portion removed to illustrate various internal components of the ring.

In other aspects, a battery 220 can be installed in the ring 202 to supply power to various components of the ring 202. The battery 220 may be designed to supply power to the ring 202 for a period from three to five days or as many as seven days, for example, without recharging the battery 220. In one embodiment, charging of the battery 220 may be enabled via a pre-loaded battery-charger. In one mode, the charger can be fixed on top of the ring 202 through mechanical and magnetic tools 222, for example, and connected to the ring battery 220 through a top portion of the ring 202 (as shown in FIG. 2C, for example). In other embodiments, the battery 220 can be powered and recharged through a separate power loading station, or a battery pack (preloaded) which can be contacted to the ring 202, and which allows the ring 202 to continue health performance measurements during the power recharging process. In case of low power or loss of power the data are safe due to a non-volatile storage.

Figure 6A:
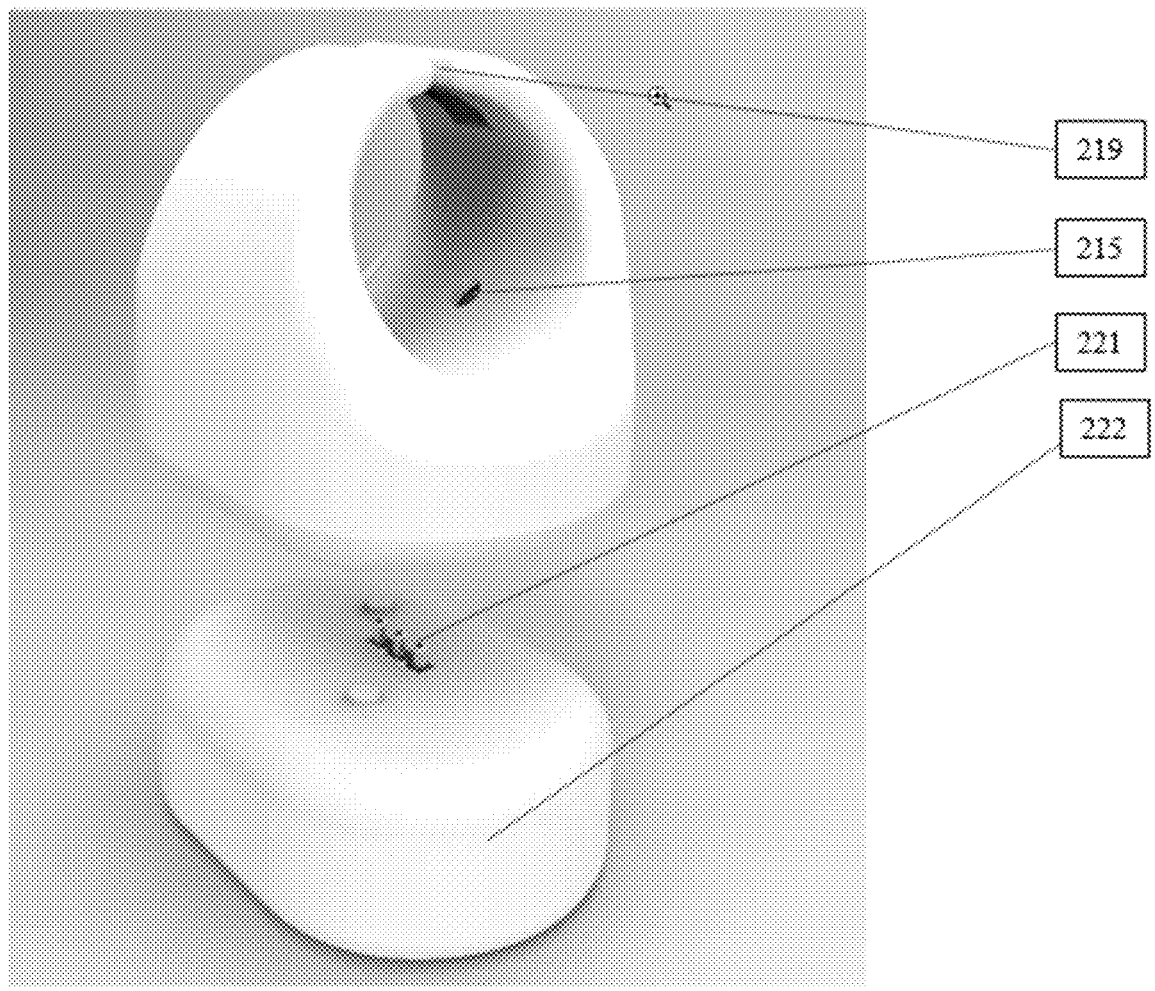
FIG. 6A is a three-dimensional view of one example of a ring-type wearable device and a battery charger device.
Figure 6B:
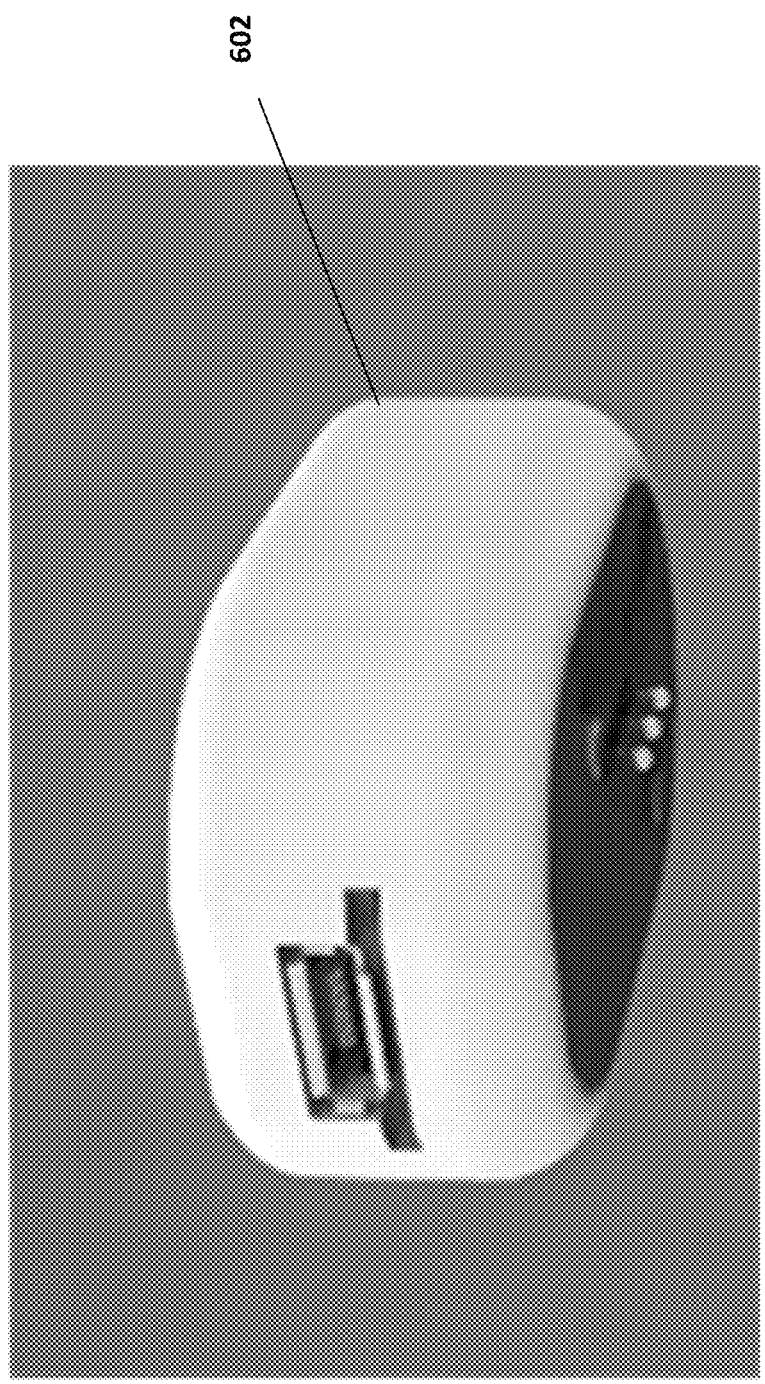
FIG. 6B is a three-dimensional view of the battery charger device of FIG. 6A.
Figure 6C:
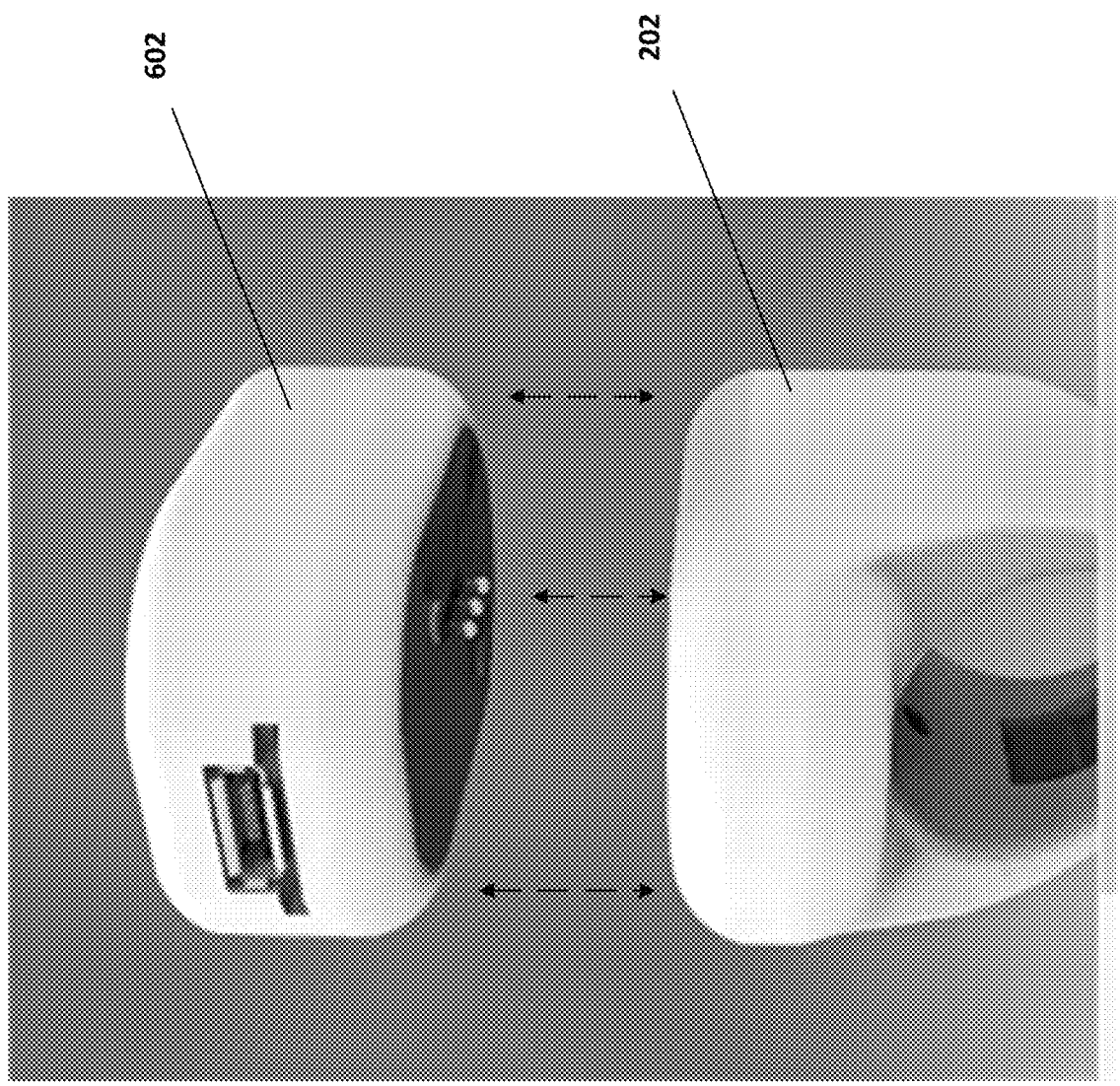
FIG. 6C depicts another view of the ring and battery charger combination of FIG. 6A.
Figure 6D:
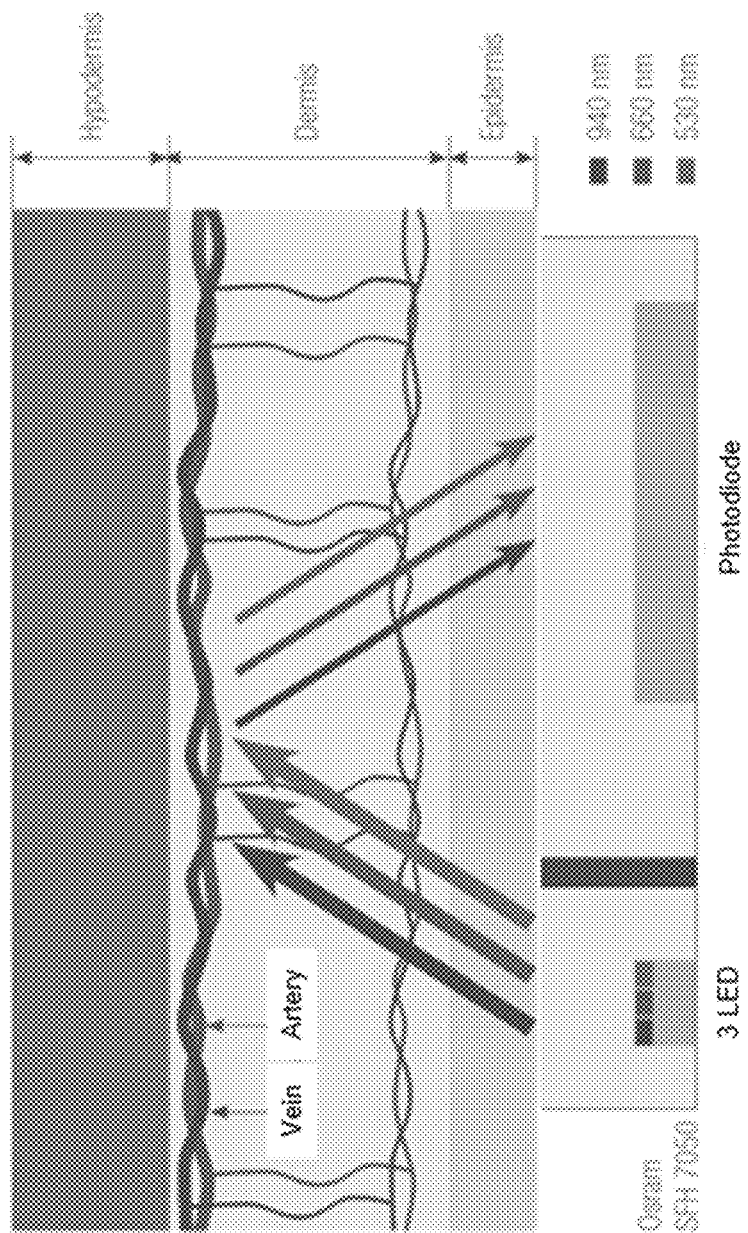
FIG. 6D schematically illustrates an example of interaction of a light sensor system with the body of a ring wearer.
Figure 6E:
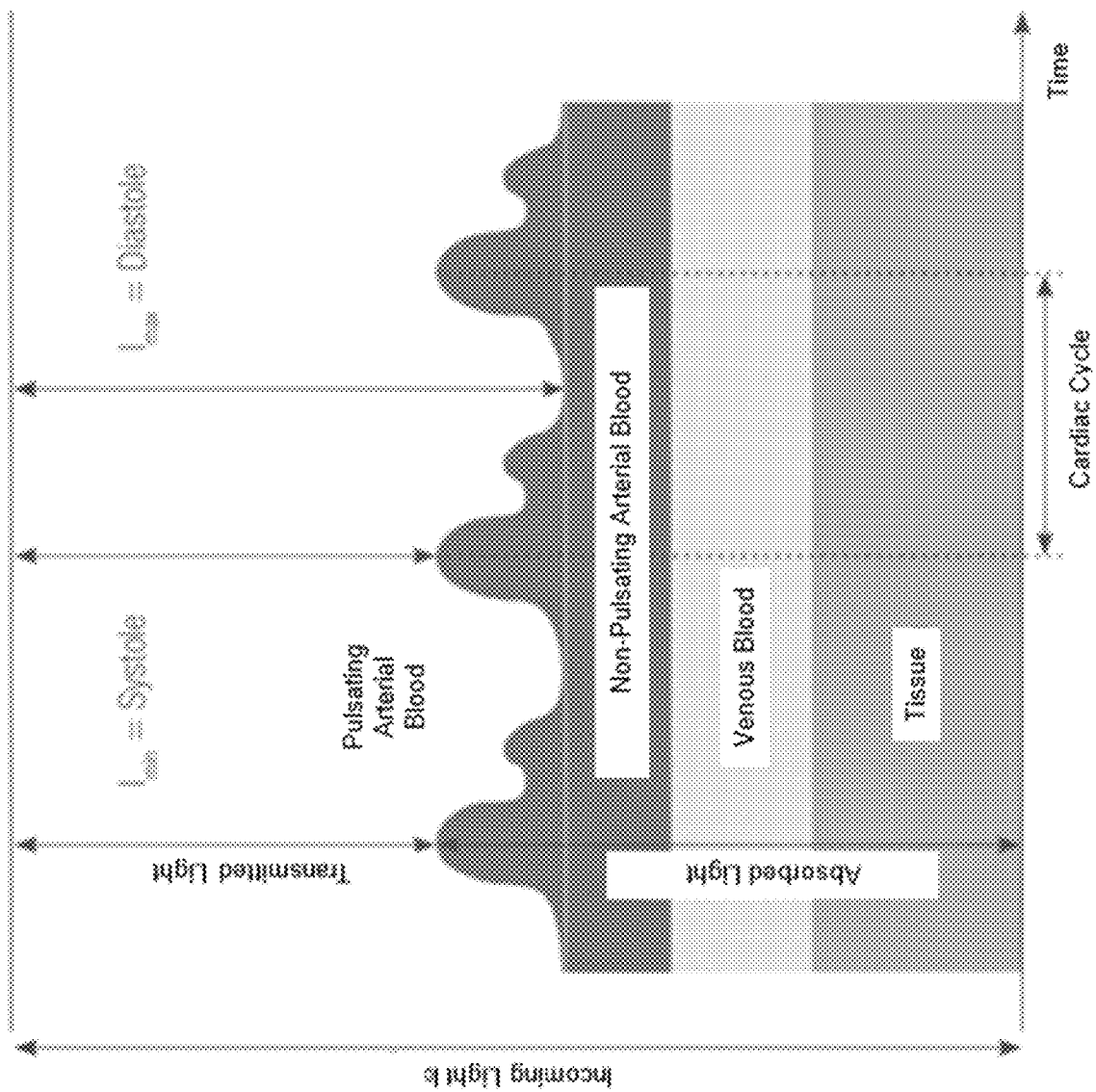
FIG. 6E schematically illustrates another example of interaction of a light sensor system with the body of a ring wearer.

FIGS. 6B and 6C illustrate an example of a charger 602 which can be used in operative connection with the ring 202. It can be seen how the processes of charging a battery of the charger 602 and/or charging the ring 202 battery can be performed with little or no significant interruption of biometric data collection performed by the ring 202.

It can be appreciated that the innovative design concept embodied by the present invention provides a wearable ring 202, instead of a wrist band, and the wearable ring 202 does not need a screen which can be difficult for a user to see and access. Measured health performance data can be temporarily stored within the ring 202 for subsequent download to an external data storage medium, and the health performance of the user can be measured automatically and continuously over time. The definition of what "continuous" measurement means can be defined through a setting provided in an installation program. In one aspect, the temporarily stored data in the ring 202 can be transferred through low energy Bluetooth (BLE), for example, to a smart device and uploaded to a cloud computing environment. The data can be visualized and reviewed through the access device by the user, and/or sent to a family member or caregiver, for example.

Human skin types (darker or brighter pigments) can impact the absorption of LED light on the skin surface. Different available LED light wavelengths with different absorption coefficients allow for analysis of different skin types. The inventors have discovered that there is less impact to the effect of signal quality on this analysis if the intensity of light is strong enough. It is comparatively more important to maintain continuous or substantially continuous contact between the LEDs and the skin. In reflection mode, in particular, the pressure of the LED-to-skin contact has a comparatively stronger impact on the signal/noise intensity. In transmission mode, the pressure of the LED on the skin has a comparatively lower impact on the quality of the measured biometric data.

Sleep and nap detection can be performed in connection with operation of the accelerometer (e.g., which may be a 6D accelerometer) and the function of the light sensor system (e.g., in connection with measuring heart frequency signal). Detection of movement and/or exercise, sleeping or napping, and awake phase can be detected by the accelerometer (e.g., as movement over time) in conjunction with determining and analyzing heart rate (e.g., signal intensity over time).

Figure 7A:
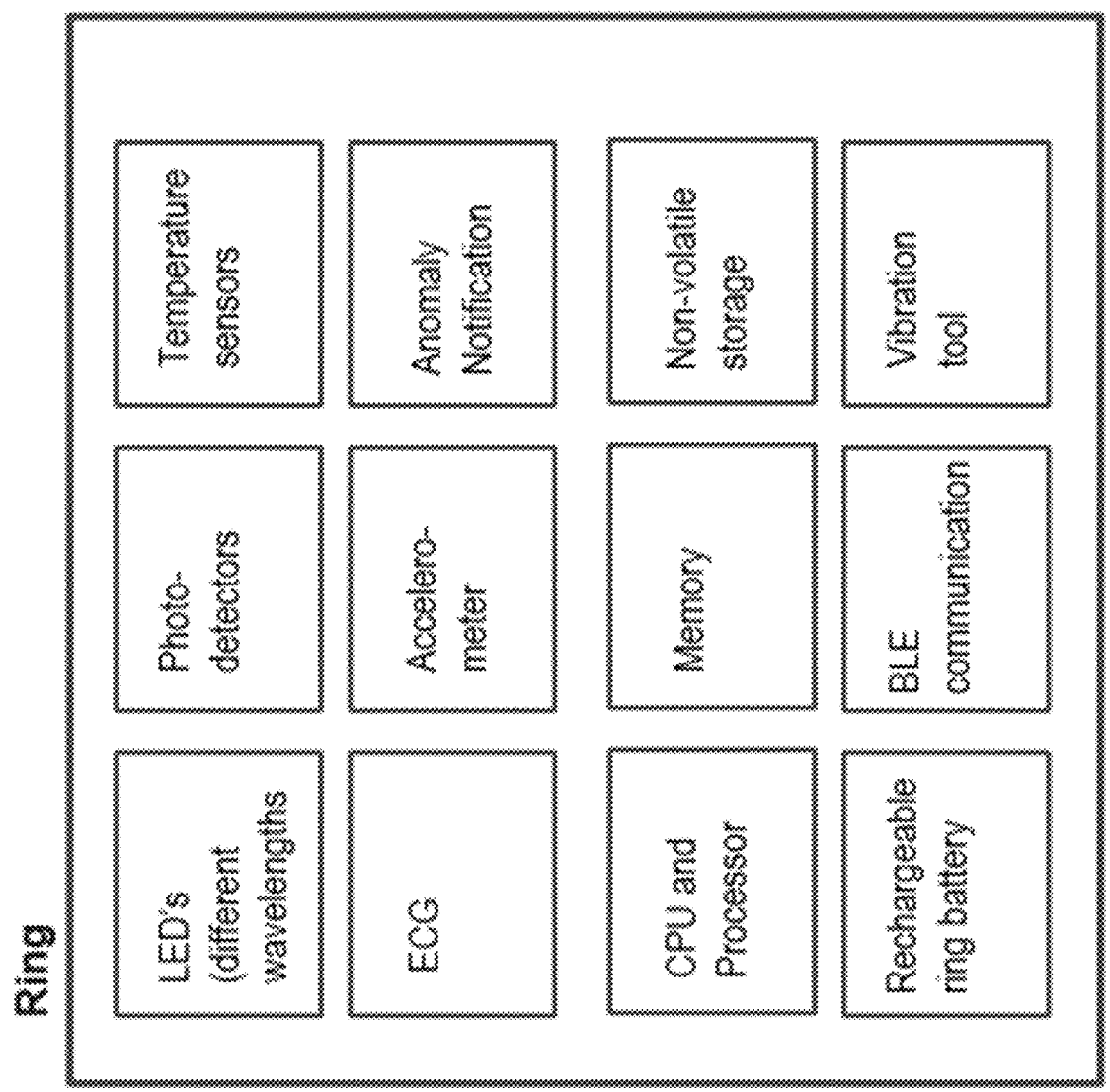
FIG. 7A schematically depicts examples of internal components which may be incorporated into one embodiment of a ring.

FIG. 7A schematically depicts examples of internal components which may be incorporated into one embodiment of a ring 202 as structured in accordance with certain embodiments of the invention.

Figure 7B:
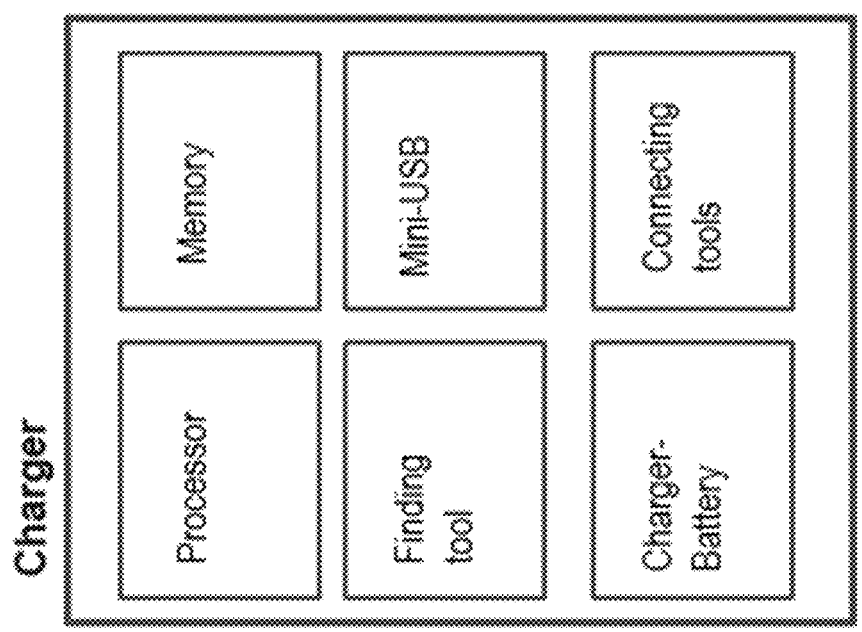
FIG. 7B schematically depicts examples of various internal components which may be incorporated into one embodiment of a battery charger for a ring.

FIG. 7B schematically depicts examples of internal components which may be incorporated into one embodiment of a charger for a ring 202 as structured in accordance with certain embodiments of the invention.

FIG. 7C illustrates examples of LED and photodetector components which can be employed by the ring devices described herein. Examples of an LED component 702 and a photodetector (photodiode) component 704 are shown.

Figure 8A:
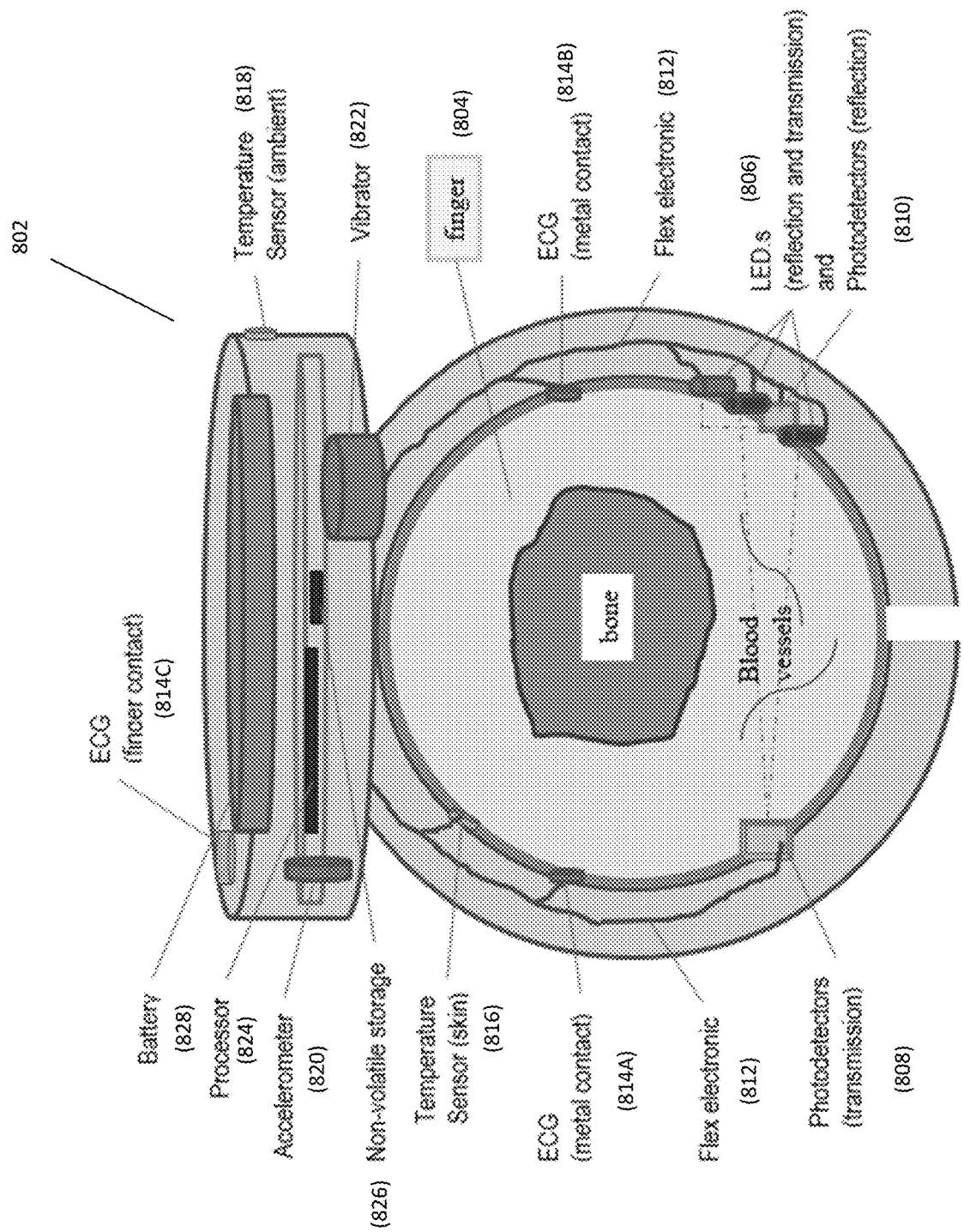
FIG. 8A schematically illustrates, with a partially cutaway view, an example of a wearable ring device.

FIG. 8A schematically illustrates, with a partially cut-away view, an example of the wearable ring device 802 including its various components: sensors, data management components, and power management components, as worn on the finger 804 of a user. In this example, a light sensor system includes LEDs 806 configured for both transmissive and reflective modes of operation in conjunction with photodetectors 808 (transmission) and photodetectors 810 (reflection). Flex electronic 812 provides a substrate for electrically connecting LEDs 806, while promoting their contact with the finger 804 of the user. In connection with performing ECG measurements, metal contacts 814A, 814B are positioned to contact the skin of the finger 804, and to form an electrical circuit with finger metal contact 814C. In this manner, when finger contact 814C is pressed by the ring 802 wearer, an electrical circuit is completed and an ECG measurement can be facilitated.

In other aspects of the ring 802, skin temperature sensor 816 provides another important biometric measurement, while ambient temperature sensor 818 provides an indication of the temperature in the environment surrounding the ring 802. Accelerometer 820 can be employed to determine changes in motion of the ring 802, perhaps as the wearer is moving and can provide an indication of a fall or other movement outside of an expected range. Vibrator 822 can be used to generate a notification to the ring 802 wearer, such as when the system detects an anomaly in the wearer's biometric data. A processor 824 or chip set can receive and process data signals collected by the various sensors of the ring 802, while controlling or directing execution of various kinds of tasks within the ring 802. For example, the processor 824 can direct storage of certain processed or unprocessed data in a non-volatile storage medium 826. Such non-volatile storage can be especially useful for retaining biometric data in the event of a power loss or disruption experienced by a battery 828 of the ring 802, for example.

Figure 8B:
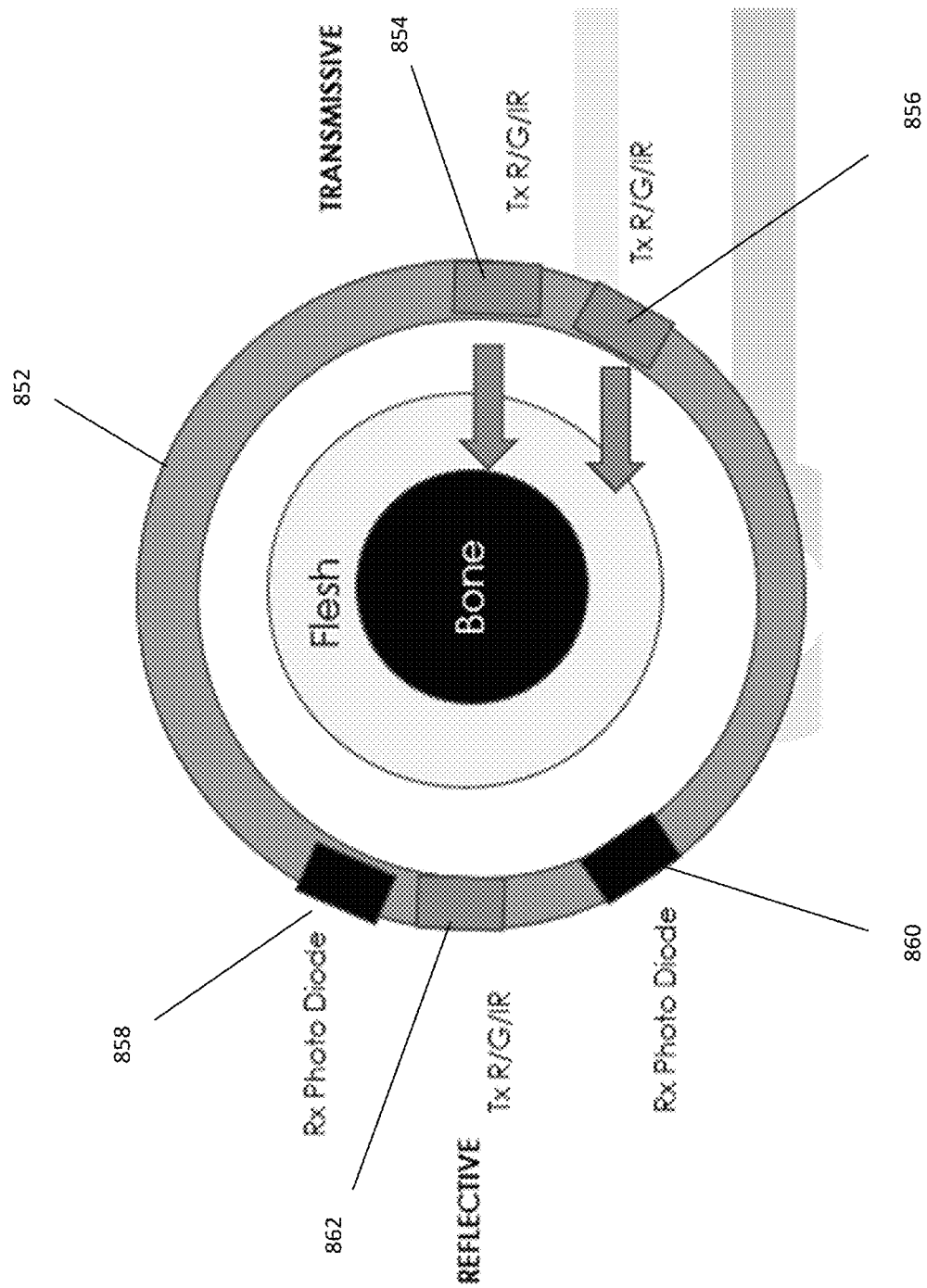
FIG. 8B schematically illustrates an example of different transmissive and reflective modes of operation of a ring device.
Figure 8C:
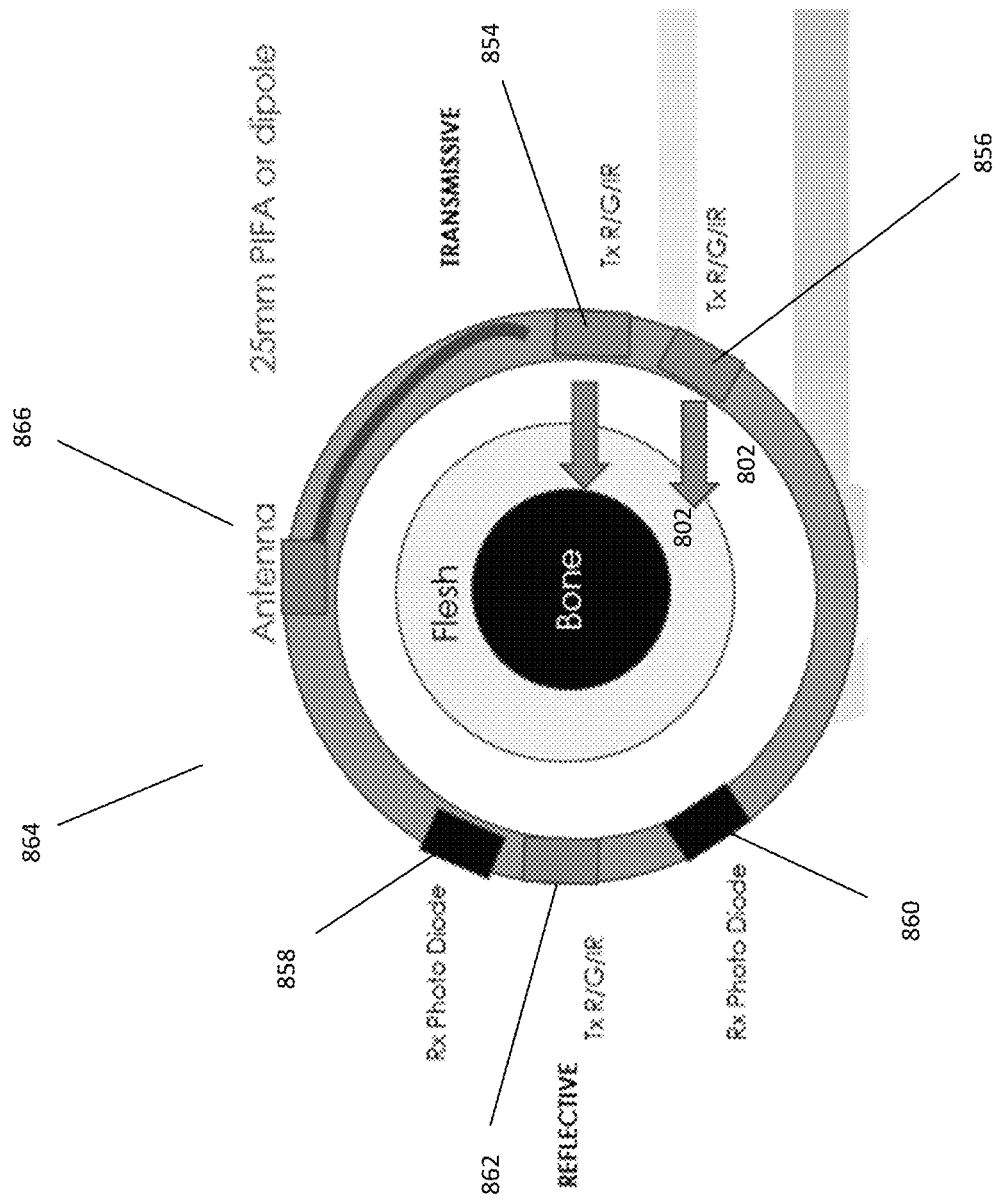
FIG. 8C depicts use of a ring having an antenna configured to communicate data sensed and collected by action of a ring device.

FIG. 8B schematically illustrates an example of the different modes of operation of a ring 852. In this example, LEDs 854, 856 operate in connection with photodetectors 858, 860 in a transmissive mode, and LED 862 operates in a reflective mode. FIG. 8C depicts use of a ring 864 having an antenna 866, which may be configured to communicate data sensed and collected by action of the ring 864. As noted above, the antenna 866 may be configured as a 2.4 GHz antenna (e.g., 25 mm PIFA or dipole), for example, to enable dual communication from the ring 864 to one or more other kinds of external computer systems on WiFi and/or BLE wireless communication protocols.

Figure 9B:
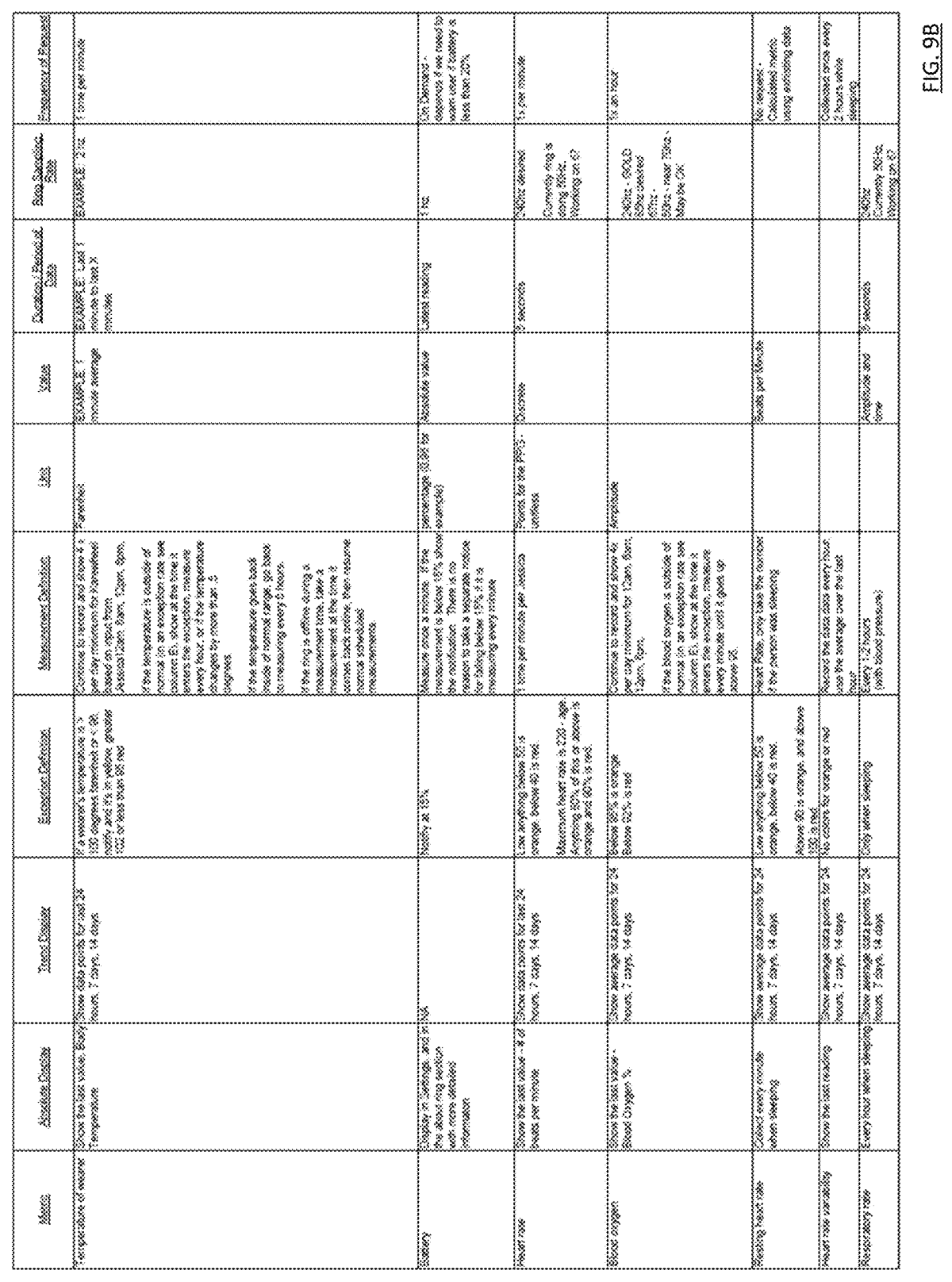
Figure 9C:
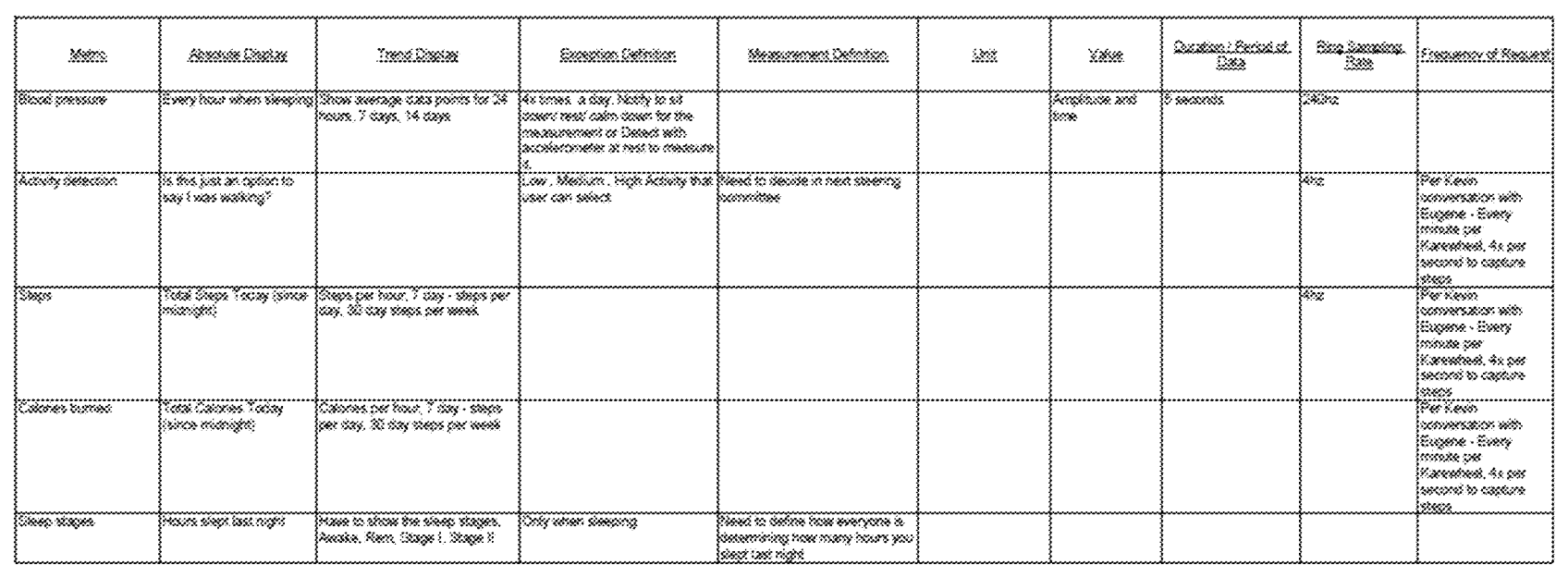

FIG. 9A depicts an overview summary of different examples of the kinds of biometric measurement data which can be sensed, collected, and then analyzed data in connection with use of the ring 202. FIGS. 9B and 9C include a table illustrating examples of different biometric data which can be collected by use of the ring 202. This includes examples of how the biometric data can be displayed on an absolute or tending basis, definitions for how the biometric measurement can be defined and executed, units and values, durations of measurement, sampling rate, and the frequency of requesting the data.

Figure 10B:
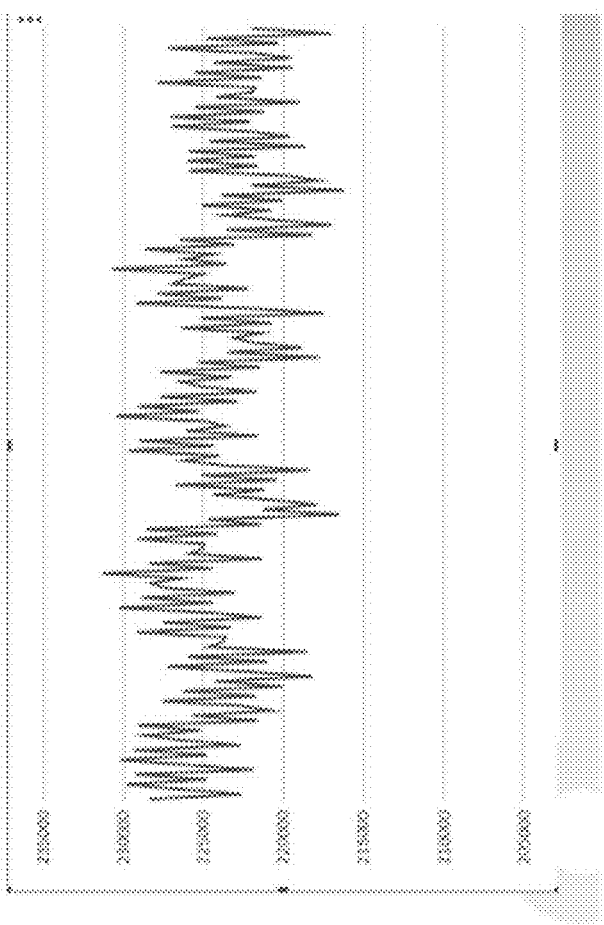
FIGS. 10A and 10B include examples of generating and displaying PPG waveforms in accordance with certain embodiments of the invention.
Figure 10A:
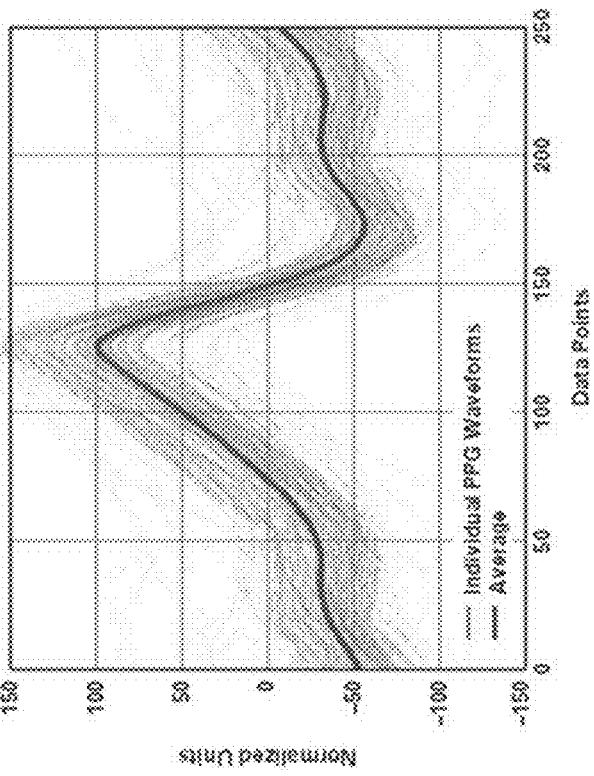

FIGS. 10A and 10B include examples of generating and displaying PPG waveforms in accordance with certain embodiments of the invention.

Figure 11:
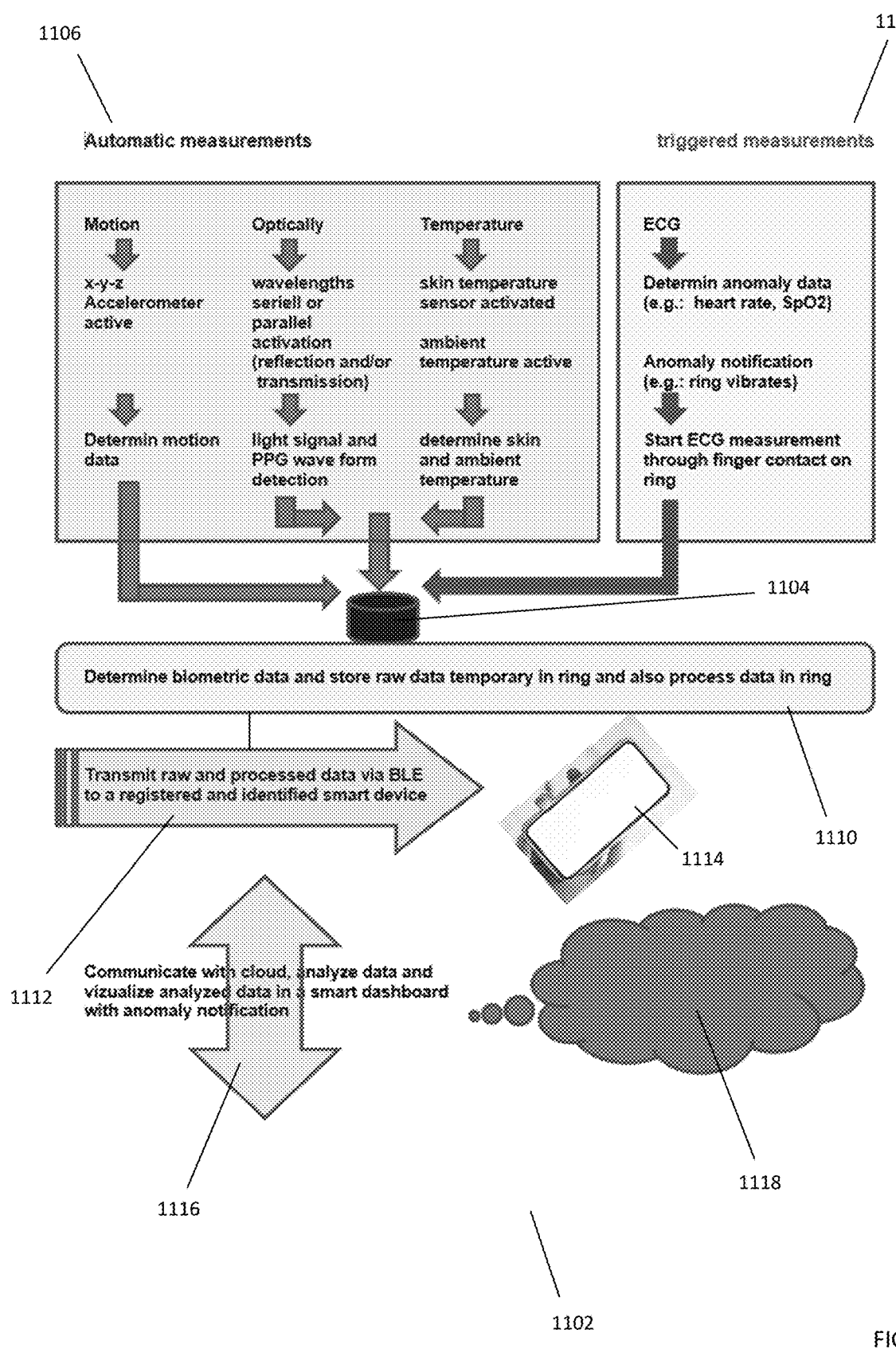
FIG. 11 illustrates an example of a computer system and certain associated process flows which embody a computing environment architecture structured for data collection, analysis, and storage in operative association with a wearable ring device.

FIG. 11 illustrates an example of a system 1102 and certain associated process flows which embody a computing environment architecture structured for automatic and triggered data collection, data analysis, data storage in the wearable sensor ring, and transmission or communication of data to mobile (smart) devices, as well as communication with a cloud computing environment. As shown, the architecture includes an example of a computer system configured and programmed to receive, analyze, and process data and signals communicated by the ring 202. In various embodiments, the computer system may include a combination of one or more processors or servers, hardware, software, firmware, and/or logic circuitry programmed to process the received signals, to analyze and store data derived from the ring configuration, and/or to direct the functions or tasks of other components in the system. The system may be further programmed to generate and display dashboards and other types of user interface screens to different users via a variety of access devices (e.g., browser interfaces, laptops, notebooks, mobile devices, etc.).

In this example, a ring 1104 is configured for use in connection with performing various automatic biometric measurements 1106, as well as certain triggered measurements 1108, as previously described herein. At step 110, biometric data can be measured, determined, or collected, and then stored in the ring 1104 as processed and/or unprocessed data. At step 1112, at least apportion of the unprocessed and/or processed data can be communicated (e.g., via a BLE protocol) to one or more kinds of access devices 1114 (e.g., mobile devices). At step 1116, at least a portion of the processed and/or unprocessed data stored in the ring 1104 can be communicated to a cloud computing system 1118 where the data can be further analyzed and/or displayed in individual-based and/or facility-based portal views. The cloud computing system 1118 can be configured for determining anomaly conditions (e.g., a biometric data value which is outside of a predetermined or desired nominal value range). The system 1118 can further generate and communicate anomaly notifications to various kinds of users in response to the determined anomaly condition. In other aspects, generation of medical grade quality biometric data can be enabled by post-processing data in the cloud computing system 1118.

Figure 12:
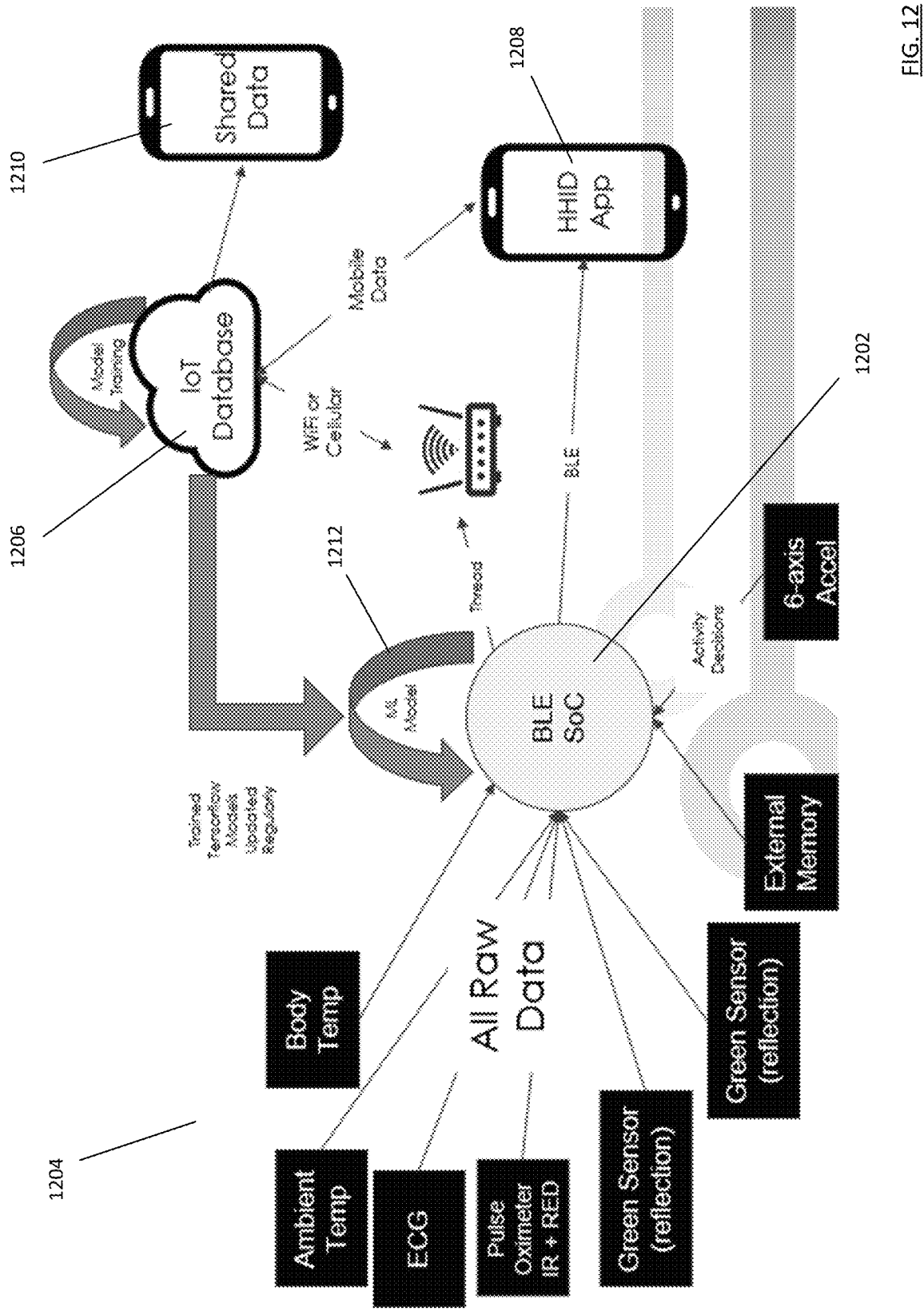
FIG. 12 illustrates another example of a computer system and certain associated process flows which embody a computing environment architecture structured for data collection, analysis, and storage in operative association with a wearable ring device.
Figure 13:
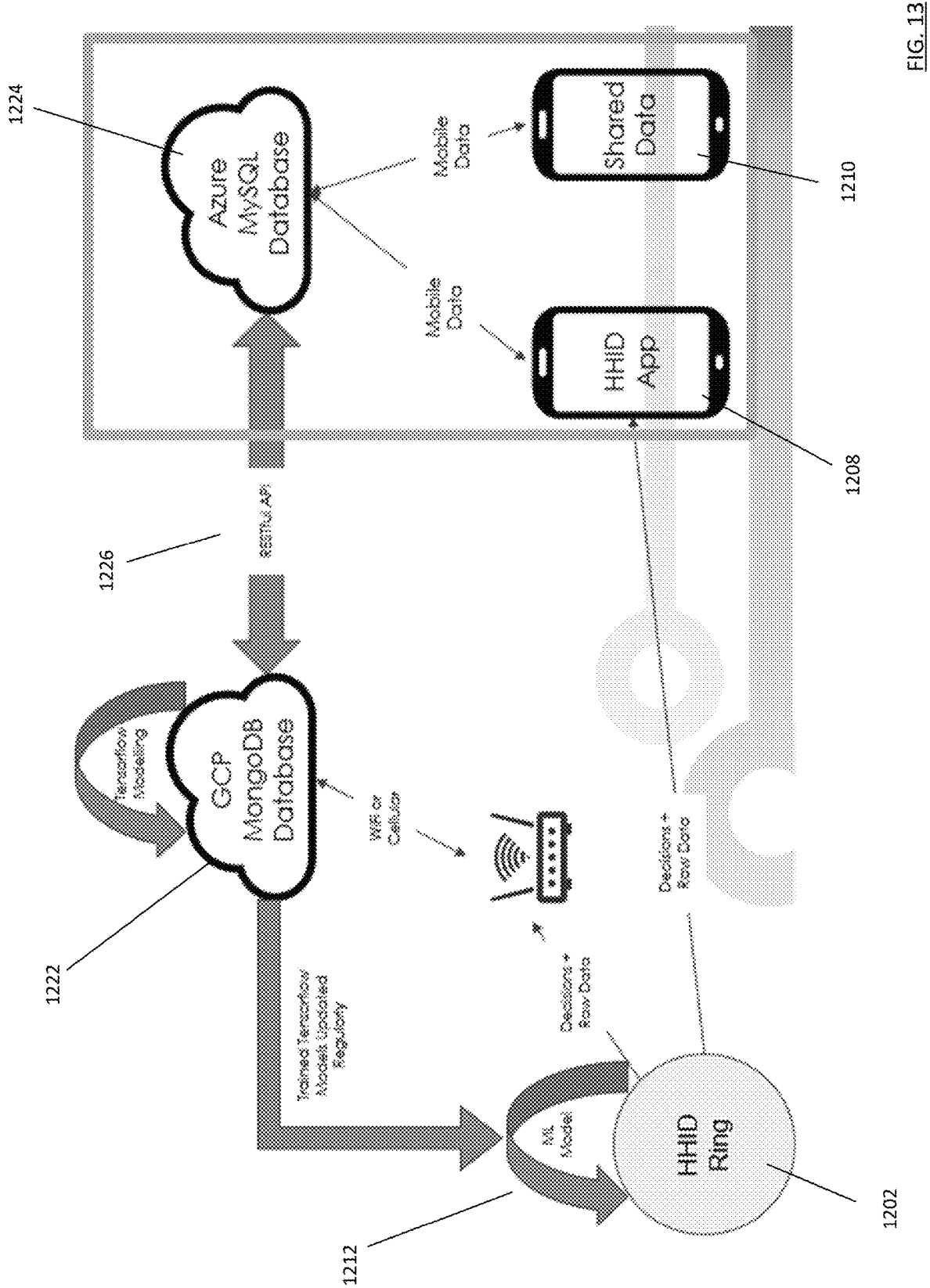
FIG. 13 illustrates another example of a computer system and certain associated process flows which embody a computing environment architecture structured for data collection, analysis, and storage in operative association with a wearable ring device.

FIGS. 12 and 13 include other examples of computing environment architectures structured for automatic and manual trigger data collection, data analysis, transmission or communication of data to mobile devices, and communication of data with a cloud computing environment.

As shown in FIG. 12, a ring 1202 is configured and programmed to collect and process data derived from various sensor devices 1204 operatively associated with the ring 1202. At least a portion of processed and/or unprocessed data may be communicated from the ring 1202 via a WiFi or cellular wireless communication protocol to an IoT database 1206, and/or via a BLE communication protocol to one or more kinds of access devices 1208. The database 1206 may be configured to provide shared data with other access devices 1210 (e.g., associated with relatives or health care facilities), as may be permitted by the wearer of the ring 1202. The database 1206 can be configured to operate in connection with a machine learning (ML) model 1212 (e.g., a TensorFlow model) to develop machine learning algorithms based on collected data. Machine learning algorithms developed by the model 1212 can be used to communicate executable instructions to the ring 1202 in connection with the data collection and analysis functions of the ring 1202.

Figure 14:
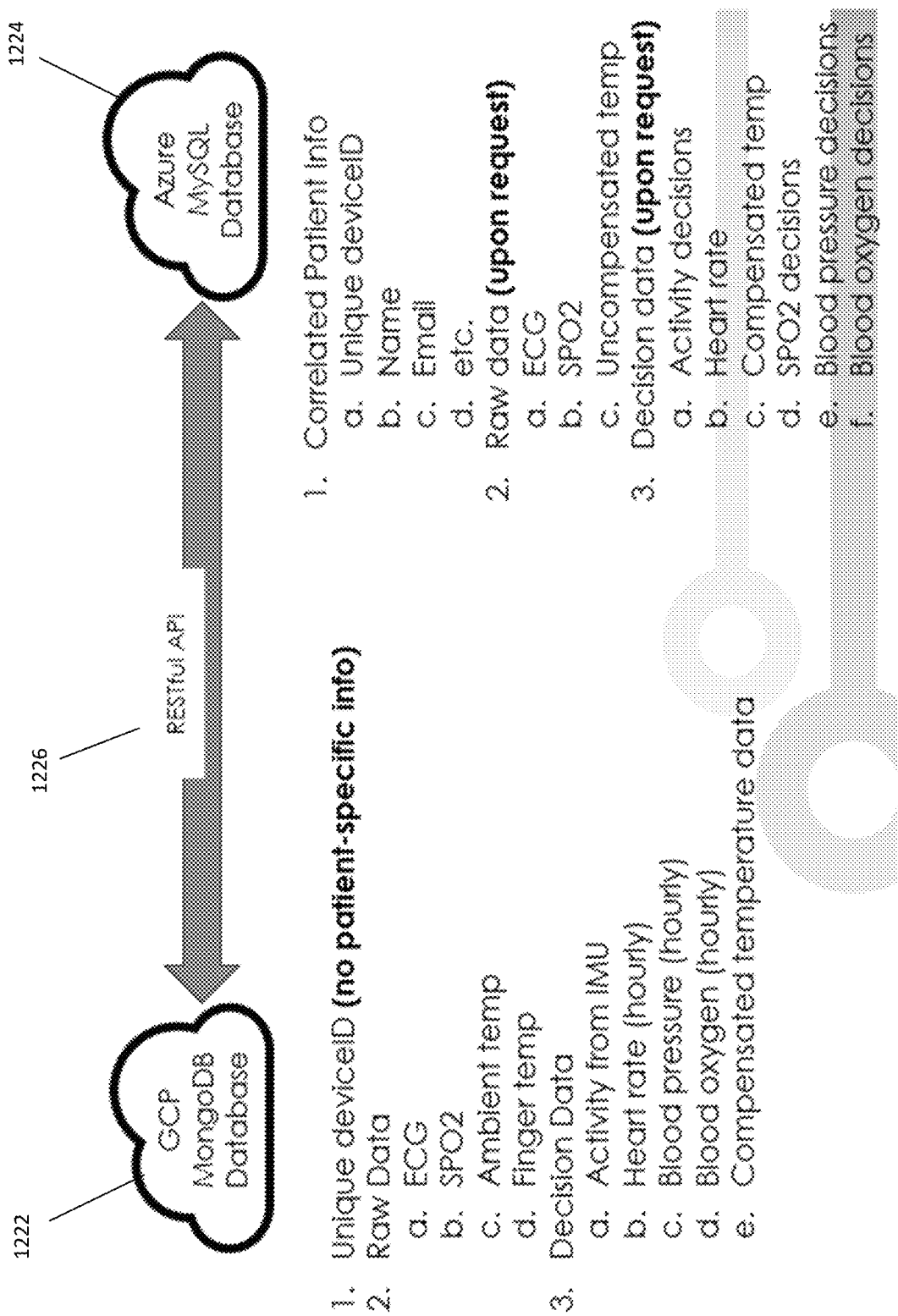
FIG. 14 schematically illustrates an example of a strategy for enabling data communications between multiple databases functioning in a computing environment architecture structured for data collection, analysis, and storage in operative association with a wearable ring device.

FIG. 13 illustrates an example of an interaction between the multiple databases 1222, 1224, communicating through a communications interface 1226 (e.g., RESTful API). Relational database 1224 (e.g., Azure SQL database) can be configured to provide relational database services related to cloud computing processes. Database 1222 (e.g., MongoDB database) can be configured as a source-available cross-platform document-oriented database program, which can use JSON-like documents with optional schemas. FIG. 14 schematically illustrates a strategy for enabling data communications between multiple databases 1222, 1224, as implemented by one example of a computer architecture which may be employed in connection with certain embodiments of the invention. As shown, an IoT database can store large raw data sets and decision data. Also, the communication interface 1226 can accommodate mobile and web applications associated with operation and use of different ring devices.

Figure 15:
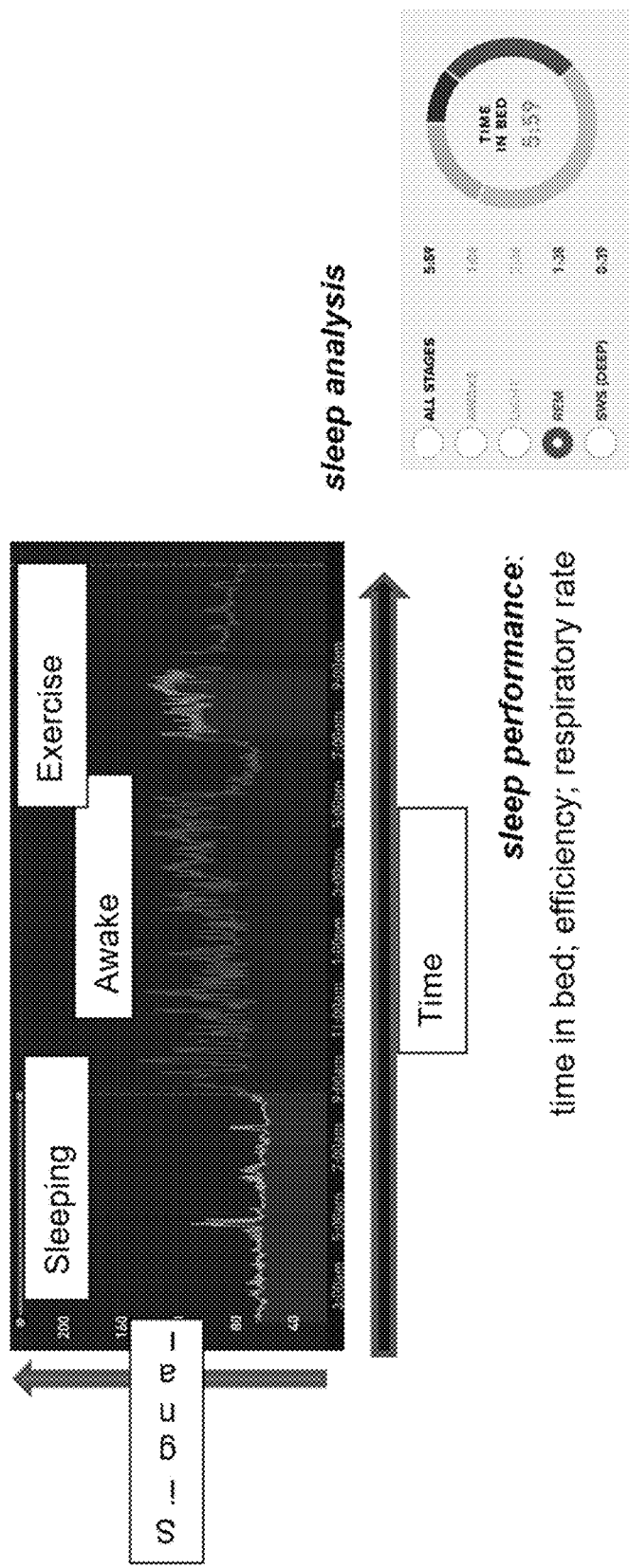
FIG. 15 illustrates an example of how other types of detected and processed data obtained from a ring can be graphically presented to a user.

FIG. 15 illustrates an example of how other types of detected and processed data obtained from the ring 202 can be graphically presented to a user. In this example, sleep-related condition data can be collected with the ring 202, such as during the sleep cycles of a wearer of the ring 202.

Figure 16:
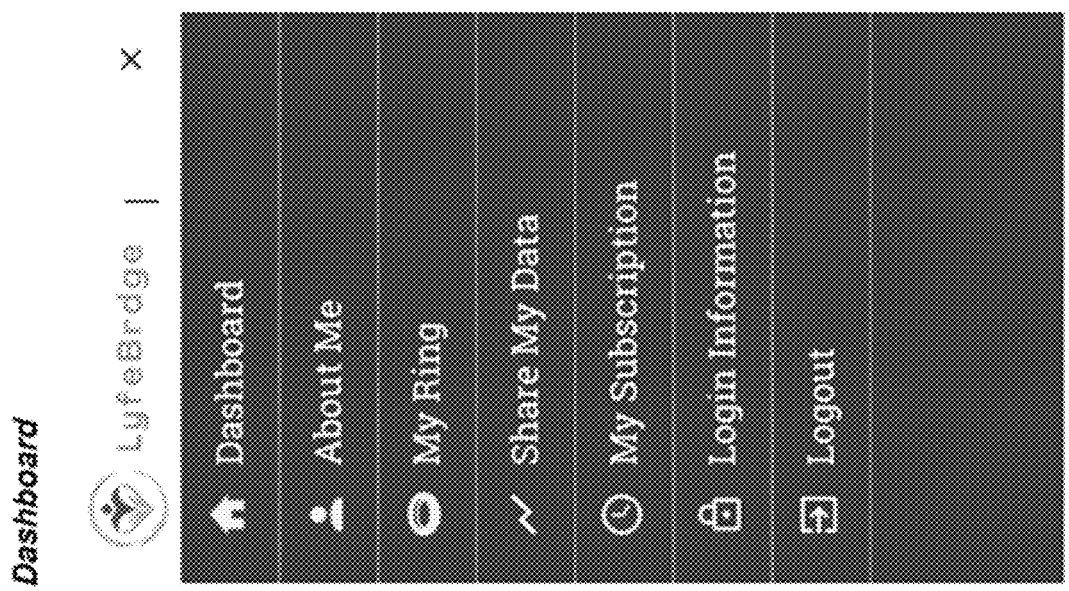
FIG. 16 is a wireframe representation of one example of a dashboard user interface screen which can be generated and displayed on a user access device.
Figures 17, 18, 19:
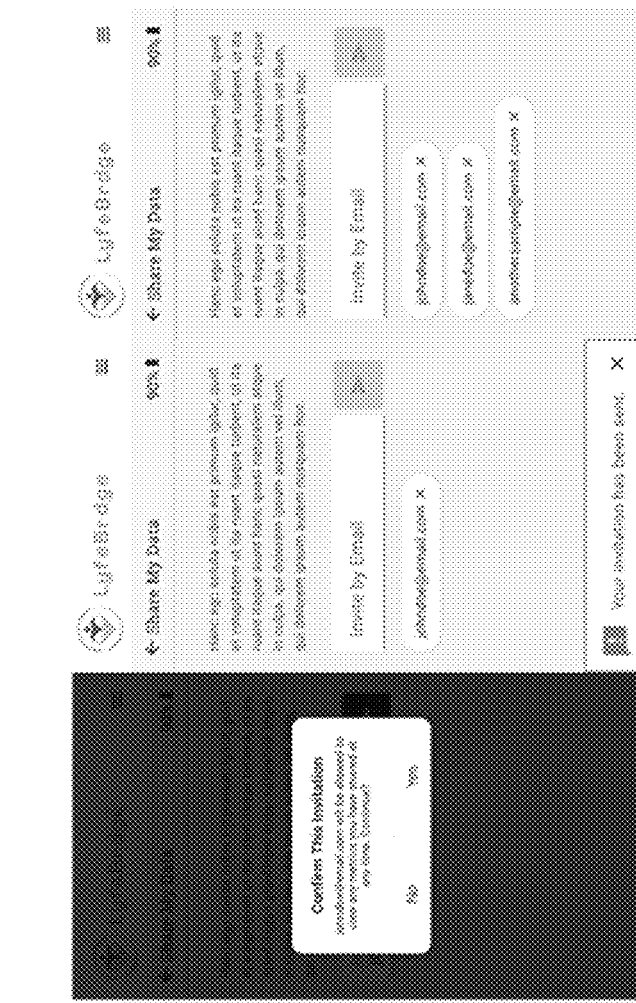
Figures 20, 21:
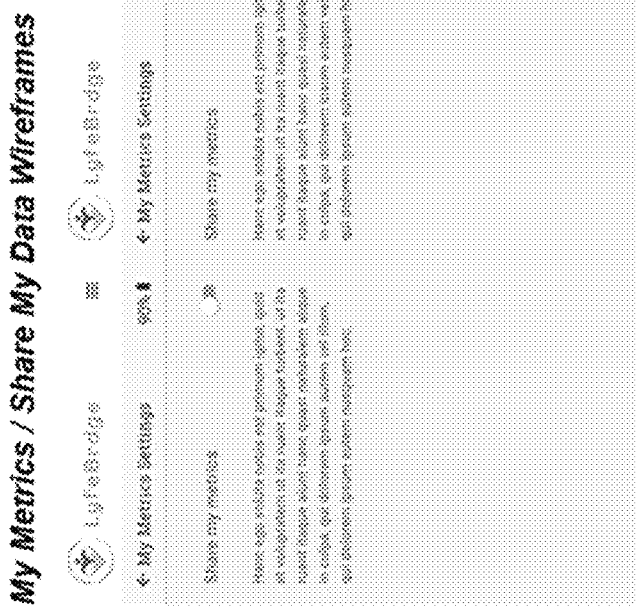
Figures 22, 23, 24, 25:
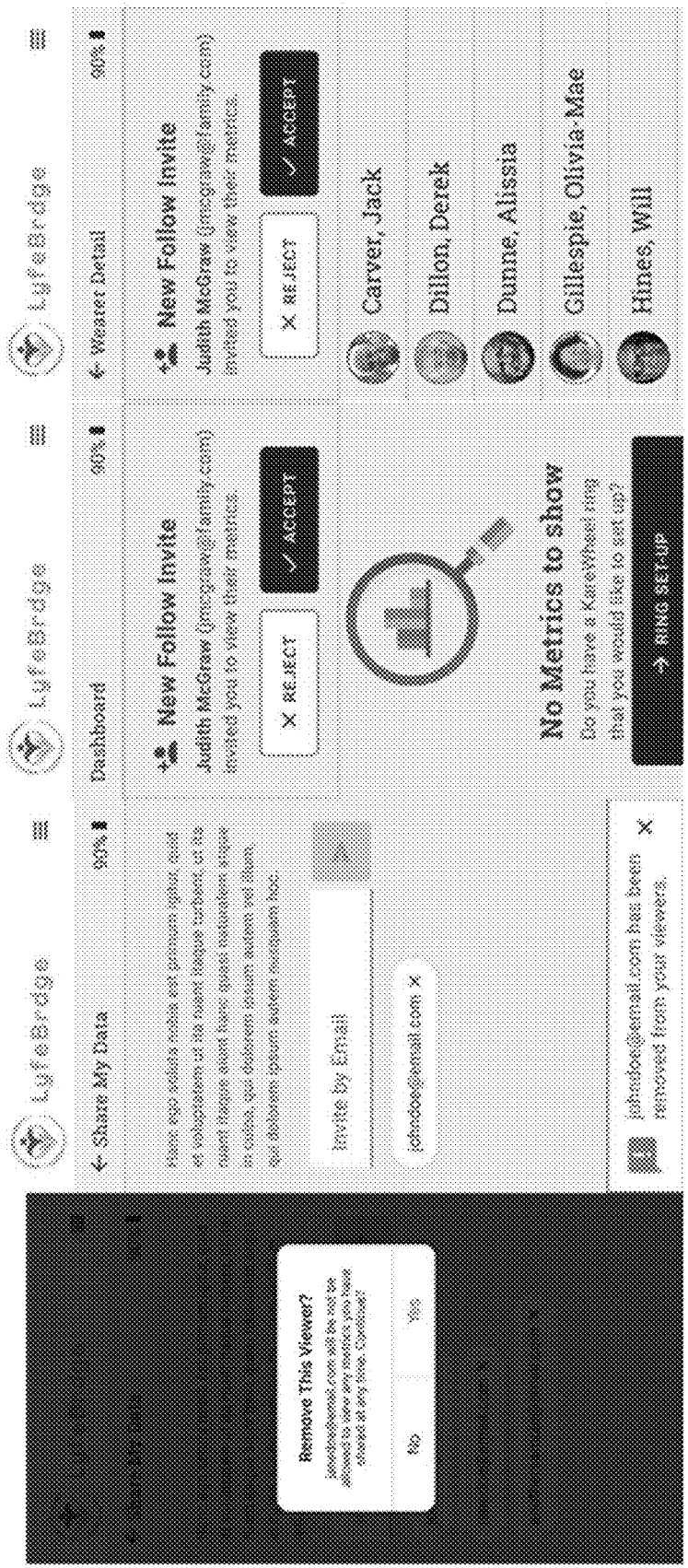
Figures 26, 27, 28, 29, 30:

FIG. 16 is a wireframe representation of one example of a user interface screen which can be generated and displayed on a user access device (e.g., laptop, mobile phone, notepad, etc.). In this example, a dashboard is presented through which various aspects of ring device operation and use can be accessed by the user, including sections for About Me, My Ring, Share My Data, My Subscription, and/or Login Information. For example, certain user interfaces accessible through the dashboard may provide screens which provide information about the wearer of the ring (name, date of birth, gender, etc.). Other user interface screens may provide account or subscription information.

FIGS. 17 through 32 include various wireframe representations of examples of user interface screens which can be generated and displayed on a user access device to show "My Metrics" and/or "Share My Data" information for the ring device. An interface can be displayed which provides the ability to link the ring device to an email account, to share information to multiple email accounts, to add emails of people who will be receiving the information, to remove emails of people who will no longer be receiving information, to invite others to link to the ring device by email, confirm invitation to linking to the ring device by email, and/or display if the metrics are to be shared or not shared. Emails can be documented and stored as desired, although other suitable methods of communication other than email may be employed in connection with certain embodiments of the invention. As shown, other user interface screens display information about the metrics of the wearer of the ring. Such metrics may include heart rate, resting heart rate (e.g., lowest heart for the day), heart rate variability, blood oxygen level, blood pressure, temperature, respiratory rate, activity detection, steps, calories burned, and/or sleep stages.

FIGS. 33 through 37 include various wireframe representations of examples of user interface screens which can be generated and displayed on a user access device to show "My Ring" information for the ring device. This information may include, for example, a screen which provides information about the ring device, setup and connection data, association of the ring device to an account, battery usage (e.g., percentage), and/or other aspects of ring device use or operation.

FIGS. 38 through 43 include various wireframe representations of examples of user interface screens which can be generated and displayed on a user access device to show user login information and procedures.

FIGS. 44 through 47 include various wireframe representations of examples of user interface screens which can be generated and displayed on a user access device to show firmware updates. Such firmware updates may be initiated through connectivity of the ring device with a cloud computing system.

It can be seen that the user interface screens of FIGS. 16 through 47 provide one example of a business to consumer (B2C) interaction and communications involving the ring device. In another example, a user interface screen shown in FIG. 48 illustrates an example of a facility portal view for data obtained from multiple rings associated with a patient population. In this example, the facility may be a health care facility treating various patients, and the portal view enables monitoring for multiple patients. In one aspect, anomaly notifications can be generated for any patients whose ring data is outside of expected or predetermined ranges. The anomaly notifications may be characterized as comparatively more severe or comparatively less severe, as shown. The portal view can employ various filters to sort and view the patient population by age, gender, or recent exception status, among other attributes.

Those skilled in the art will appreciate the important benefits of the many unique aspects of the wearable ring-type sensor devices described herein. The ECG function in the wearable sensor ring can provided important insights into the heart condition and activity of the ring wearer. Unlike other conventional devices, the rings can be used to perform continuous measurement and analysis of temperature, e.g., both skin temperature and ambient temperature. Certain computer systems described herein can generate and display smart dashboards with anomaly notifications in connection with use of the sensor ring. A vibration tool can be coupled with the anomaly notification function for providing user feedback. A charger can be provided with a battery which can be pre-charged (e.g., via micro-USB). The charger can be structured to be placed on a top portion of the sensor ring, for example, to charge the ring battery when the ring is in use. In other aspects, specific locations and positioning for LED's and light detectors in the sensor ring can be optimized to interact with the lower part of the ring wearer's finger. This can allow red and infrared light to pass through the blood stream of a ring wearer without touching the bone.

The sensor ring is flexibly structured to accommodate different finger sizes of different wearers. In other aspects, the flexible electronic structures enable the LED's and light detectors to achieve accurate positioning and optimized data collection and analysis. In certain embodiments, BLE communications (e.g., low-energy Bluetooth) transmit data comparatively more energy efficiently than other types of sensor devices. The data security aspects of the sensor rings, including its use of non-volatile data storage (e.g., minimum one day of temporary storage of data in the ring), allow for retaining data availability even if ring power is disrupted or lost. The design of the present sensor ring can be water resistant which facilitates cleaning and disinfecting the sensor ring for sterilization purposes, for example. In certain embodiments, the ring apparatus may be structured and configured to be IP67 rated, for example, with respect to having an enclosure which offers substantial protection against liquid ingress.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. For example, no particular aspect or aspects of the examples of system architectures, configurations, user interface screens, data definitions, or process flows described herein are necessarily intended to limit the scope of the invention, unless such aspects are specifically included in the claims.

Any element expressed herein as a means for performing a specified function is intended to encompass any way of performing that function including, for example, a combination of elements that performs that function. Furthermore, the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein.

In various embodiments, various models or platforms can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud computing techniques may be employed in connection with various embodiments of the invention.

Moreover, the processes associated with the present embodiments may be executed by programmable equipment, such as computers. Software or other sets of instructions that may be employed to cause programmable equipment to execute the processes may be stored in any storage device, such as a computer system (non-volatile) memory. Furthermore, some of the processes may be programmed when the computer system is manufactured or via a computer-readable memory storage medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary. Memory and/or storage components may be implemented using any computer-readable media capable of storing data such as volatile or non-volatile memory, removable or non-removable memory, erasable or non-erasable memory, writeable or re-writeable memory, and so forth. Examples of computer-readable storage media may include, without limitation, RAM, dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other type of media suitable for storing information.

A "computer," "computer system," "computing apparatus," "component," or "computer processor" may be, for example and without limitation, a processor, microcomputer, minicomputer, server, mainframe, laptop, personal data assistant (PDA), wireless e-mail device, smart phone, mobile phone, electronic tablet, cellular phone, pager, fax machine, scanner, or any other programmable device or computer apparatus configured to transmit, process, and/or receive data. Computer systems and computer-based devices disclosed herein may include memory and/or storage components for storing certain software applications used in obtaining, processing, and communicating information. It can be appreciated that such memory may be internal or external with respect to operation of the disclosed embodiments. In various embodiments, a "host," "engine," "loader," "filter," "platform," or "component" may include various computers or computer systems, or may include a reasonable combination of software, firmware, and/or hardware. In certain embodiments, a "module" may include software, firmware, hardware, or any reasonable combination thereof.

In various embodiments of the present invention, a single component may be replaced by multiple components, and multiple components may be replaced by a single component, to perform a given function or functions. Any of the servers described herein, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described hereinabove may be implemented in computer software using any suitable computer programming language such as .NET or HTML using, for example, conventional or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high-level languages include Ada, BASIC, C, C++, C #, COBOL, Fortran, Java, Lisp, Pascal, Object Pascal; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, power line communication or G.hn. Wireless communications described herein may be conducted with Wi-Fi and Bluetooth enabled networks and devices, among other types of suitable wireless communication protocols. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to conduct the traffic of different user communities separately and securely over an underlying network. The VPN may provide users with the virtual experience of accessing the network through an IP address location other than the actual IP address which connects the wireless device to the network. The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods and systems described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity. As applied herein, an extranet may include a network or internetwork generally limited to a primary organization or entity, but which also has limited connections to the networks of one or more other trusted organizations or entities (e.g., customers of an entity may be given access an intranet of the entity thereby creating an extranet).

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs); remote bridges can be used to create a wide area network (WAN) link between LANs; and/or, wireless bridges can be used to connect LANs and/or to connect remote stations to LANs.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to manage simultaneous execution of multiple computer programs.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a processor or application specific processor.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. Discrete components and features may be readily separated from or combined with the features of any of the other several aspects without departing from the scope of the present disclosure. Any recited method can be conducted in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

Certain embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It will be appreciated that those skilled in the art will be able to devise various arrangements which, although not explicitly described or shown herein, embody the principles of the present disclosure and are comprised within the scope thereof. Furthermore, all examples and conditional language recited herein are principally intended to aid the reader in understanding the principles described in the present disclosure and the concepts contributed to furthering the art and are to be construed as being without limitation to such specifically recited examples and conditions. Moreover, all statements herein reciting principles, aspects, and embodiments as well as specific examples thereof, are intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

Although various systems described herein may be embodied in software or code executed by hardware as discussed above, as an alternative the same may also be embodied in dedicated hardware or a combination of software/hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc.

The flow charts and methods described herein show the functionality and operation of various implementations. If embodied in software, each block, step, or action may represent a module, segment, or portion of code that comprises program instructions to implement the specified logical functions. The program instructions may be embodied in the form of source code that comprises human-readable statements written in a programming language or machine code that comprises numerical instructions recognizable by a suitable execution system such as a processing component in a computer system. If embodied in hardware, each block may represent a circuit or a number of interconnected circuits to implement the specified logical functions.

Reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment. The terms "a" and "an" and "the" and similar referents used in the context of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as" or "for example") provided herein is intended merely to better illuminate the disclosed embodiments and does not pose a limitation on the scope otherwise claimed. No language in the specification should be construed as indicating any non-claimed element essential to the practice of the claimed subject matter. It is further noted that the claims may be drafted to exclude any optional element. As such, this statement is intended to serve as antecedent basis for use of such exclusive terminology as solely, only and the like in connection with the recitation of claim elements, or use of a negative limitation.

Groupings of alternative elements or embodiments disclosed herein are not to be construed as limitations. Each group member may be referred to and claimed individually or in any combination with other members of the group or other elements found herein. It is anticipated that one or more members of a group may be comprised in, or deleted from, a group for reasons of convenience and/or patentability.

In various embodiments of the present invention, different types of artificial intelligence tools and techniques can be incorporated and implemented. Search and optimization tools including search algorithms, mathematical optimization, and evolutionary computation methods can be used for intelligently searching through many possible solutions. For example, logical operations can involve searching for a path that leads from premises to conclusions, where each step is the application of an inference rule. Planning algorithms can search through trees of goals and subgoals, attempting to find a path to a target goal, in a process called means-ends analysis.

Heuristics can be used that prioritize choices in favor of those more likely to reach a goal and to do so in a shorter number of steps. In some search methodologies heuristics can also serve to eliminate some choices unlikely to lead to a goal. Heuristics can supply a computer system with a best estimate for the path on which the solution lies. Heuristics can limit the search for solutions into a smaller sample size, thereby increasing overall computer system processing efficiency.

Propositional logic can be used which involves truth functions such as "or" and "not" search terms, and first-order logic can add quantifiers and predicates, and can express facts about objects, their properties, and their relationships with each other. Fuzzy logic assigns a degree of truth (e.g., between 0 and 1) to vague statements which may be too linguistically imprecise to be completely true or false. Default logics, non-monotonic logics and circumscription are forms of logic designed to help with default reasoning and the qualification problem. Several extensions of logic can be used to address specific domains of knowledge, such as description logics, situation calculus, event calculus and fluent calculus (for representing events and time), causal calculus, belief calculus (belief revision); and modal logics. Logic for modeling contradictory or inconsistent statements arising in multi-agent systems can also be used, such as paraconsistent logics.

Probabilistic methods can be applied for uncertain reasoning, such as Bayesian networks, hidden Markov models, Kalman filters, particle filters, decision theory, and utility theory. These tools and techniques help the system execute algorithms with incomplete or uncertain information. Bayesian networks are tools that can be used for various problems: reasoning (using the Bayesian inference algorithm), learning (using the expectation-maximization algorithm), planning (using decision networks), and perception (using dynamic Bayesian networks). Probabilistic algorithms can be used for filtering, prediction, smoothing and finding explanations for streams of data, helping perception systems to analyze processes that occur over time (e.g., hidden Markov models or Kalman filters). Artificial intelligence can use the concept of utility as a measure of how valuable something is to an intelligent agent. Mathematical tools can analyze how an agent can make choices and plan, using decision theory, decision analysis, and information value theory. These tools include models such as Markov decision processes, dynamic decision networks, game theory and mechanism design.

The artificial intelligence techniques applied to embodiments of the invention may leverage classifiers and controllers. Classifiers are functions that use pattern matching to determine a closest match. They can be tuned according to examples known as observations or patterns. In supervised learning, each pattern belongs to a certain predefined class which represents a decision to be made. All of the observations combined with their class labels are known as a data set. When a new observation is received, that observation is classified based on previous experience. A classifier can be trained in various ways; there are many statistical and machine learning approaches. The decision tree is one kind of symbolic machine learning algorithm. The naive Bayes classifier is one kind of classifier useful for its scalability, in particular. Neural networks can also be used for classification. Classifier performance depends in part on the characteristics of the data to be classified, such as the data set size, distribution of samples across classes, dimensionality, and the level of noise. Model-based classifiers perform optimally when the assumed model is an optimized fit for the actual data. Otherwise, if no matching model is available, and if accuracy (rather than speed or scalability) is a primary concern, then discriminative classifiers (e.g., SVM) can be used to enhance accuracy.

A neural network is an interconnected group of nodes which can be used in connection with various embodiments of the invention, such as execution of various methods, processes, or algorithms disclosed herein. Each neuron of the neural network can accept inputs from other neurons, each of which when activated casts a weighted vote for or against whether the first neuron should activate. Learning achieved by the network involves using an algorithm to adjust these weights based on the training data. For example, one algorithm increases the weight between two connected neurons when the activation of one triggers the successful activation of another. Neurons have a continuous spectrum of activation, and neurons can process inputs in a non-linear way rather than weighing straightforward votes. Neural networks can model complex relationships between inputs and outputs or find patterns in data. They can learn continuous functions and even digital logical operations. Neural networks can be viewed as a type of mathematical optimization which performs a gradient descent on a multi-dimensional topology that was created by training the network. Another type of algorithm is a backpropagation algorithm. Other examples of learning techniques for neural networks include Hebbian learning, group method of data handling (GMDH), or competitive learning. The main categories of networks are acyclic or feedforward neural networks (where the signal passes in only one direction), and recurrent neural networks (which allow feedback and short-term memories of previous input events). Examples of feedforward networks include perceptrons, multi-layer perceptrons, and radial basis networks.

Deep learning techniques applied to various embodiments of the invention can use several layers of neurons between the network's inputs and outputs. The multiple layers can progressively extract higher-level features from the raw input. For example, in image processing, lower layers may identify edges, while higher layers may identify the concepts relevant to a human such as digits, letters, or faces. Deep learning may involve convolutional neural networks for many or all of its layers. In a convolutional layer, each neuron receives input from only a restricted area of the previous layer called the neuron's receptive field. This can substantially reduce the number of weighted connections between neurons. In a recurrent neural network, the signal will propagate through a layer more than once. A recurrent neural network (RNN) is another example of a deep learning technique which can be trained by gradient descent, for example.

While various embodiments of the invention have been described herein, it should be apparent, however, that various modifications, alterations, and adaptations to those embodiments may occur to persons skilled in the art with the attainment of some or all of the advantages of the present invention. The disclosed embodiments are therefore intended to include all such modifications, alterations, and adaptations without departing from the scope and spirit of the present invention as described and claimed herein.

The invention claimed is:

1. An apparatus comprising:
a ring body including an opening formed therethrough structured to receive a finger of a user therein;
a flexible power source positioned within the ring body, the power source configured for supplying power to at least one other component of the apparatus;
an electronic computer processor programmed for:
identifying when to collect at least one of unprocessed and/or processed biometric data of the user,
processing one or more signals detected by multiple light-emitting diodes (LEDs) of the apparatus, the signals indicative of a physiological condition of the user, and
storing at least a portion of the unprocessed biometric data and/or the processed biometric data in a memory storage medium positioned in the ring body;
a light sensor system connected to the ring body, the light sensor system comprising:
multiple medical grade LEDs, wherein each LED is associated with a predetermined light wavelength range, and wherein the multiple LEDs are positioned adjacent to each other in a first half of the ring body, and wherein the multiple LEDs comprise at least one green LED, at least one red LED, and at least one infrared LED,
a reflection photodetector array configured for light detection in a reflection mode at a first defined angle with respect to the multiple LEDs for detecting at least a portion of the light originating from the multiple LEDs and reflected from at least one main artery of the finger to the reflection photodetector array, wherein the first defined angle is uniquely defined in response to a size of the finger to optimize a path of the reflected light,
a transmission photodetector array configured for light detection in a transmission mode at a second defined angle with respect to the multiple LEDs for detecting at least a portion of the light originating from the multiple LEDs and transmitted through at least one main artery of the finger to the transmission photodetector array, wherein the second defined angle is uniquely defined in response to the finger size to optimize a path of the transmitted light, and
the light sensor system programmed for communicating signals indicative of light detected by the photodetectors to the processor;
a dual communication system positioned in the ring body, the dual communication system comprising:
a low energy Bluetooth (BLE) component positioned in the ring body, the BLE component configured for facilitating communicating at least a portion of the processed data and/or the unprocessed data from the ring body to a BLE-enabled receiver, and
a hub configured with a mesh network protocol for managing multiple devices wherein the mesh network protocol is configured to use an antenna positioned in the ring body for communicating with a wireless network for transferring at least a portion of the processed data and/or the unprocessed data to at least one external computer system; and
a data communication module positioned in the ring body, the data communication module programmed for:
combining data associated with the reflection photodetector array and data associated with the transmission photodetector array in at least one data storage medium of the ring body, and
communicating at least a portion of the unprocessed data and/or the processed data in the ring body to at least one external computer-based device programmed to display a dashboard user interface screen including at least one representation of at least a portion of the unprocessed data and/or the processed data comprising at least one waveform generated in response to a combination of both reflectance data and transmittance data of the unprocessed data and/or the processed data.

2. The apparatus of claim 1, further comprising an electrocardiogram (ECG) sensor system comprising multiple metal contacts configured for communicating signals indicative of at least one cardiological condition of the user when the metal contacts are in contact with at least a portion of skin of the user.

3. The apparatus of claim 2, wherein at least one of the multiple metal contacts is a finger contact accessible by a finger of the user for initiating an ECG measurement for the user when the apparatus is worn by the user.

4. The apparatus of claim 1, further comprising a vibrator positioned within the ring body, the vibrator programmed for vibrating in response to receiving an anomaly notification signal from the processor.

5. The apparatus of claim 1, further comprising an accelerometer positioned within the ring body, the accelerometer programmed for:
detecting at least one change in movement of the ring body; and
communicating a signal to the processor indicative of the detected change in movement.

6. The apparatus of claim 5, further comprising the processor programmed for receiving at least one signal from the accelerometer indicative of detecting a fall by the user.

7. The apparatus of claim 5, further comprising the processor programmed for receiving at least one signal from the accelerometer indicative of a sleep stage.

8. The apparatus of claim 1, further comprising a global positioning system (GPS) module positioned in the ring body.

9. The apparatus of claim 1, further comprising at least one temperature sensor positioned in the ring body.

10. The apparatus of claim 9, further comprising the temperature sensor configured to detect an ambient temperature in the environment around the ring body.

11. The apparatus of claim 9, further comprising the temperature sensor configured to detect a temperature of the user.

12. The apparatus of claim 1, further comprising an electrical charger configured for charging the power source, the charger being magnetically attachable and/or detachable from the ring body, and the charger configured for charging power source when the apparatus is in use.

13. The apparatus of claim 1, further comprising at least one non-volatile data storage medium configured for retaining at least a portion of the processed data or unprocessed data when the power supply is disrupted or drained.

14. The apparatus of claim 1, wherein at least a portion of the ring body is comprised of a resiliently flexible and/or elastic material.

15. The apparatus of claim 14, further comprising wherein:
at least a portion of the resiliently flexible and/or elastic material comprises a flexible electronic substrate, and
at least one of the multiple LEDs embedded in the flexible electronic substrate for promoting contact of the embedded LED with at least a portion of skin of the user when the apparatus is in use.

16. The apparatus of claim 1, wherein the ring body comprises a material comprising at least one or more of a scratch-resistant material, a hypoallergenic material, and/or a water resistant material.

17. The apparatus of claim 1, wherein at least a portion of the communicated data comprise data indicative of signals collected by the light sensor system and the processor is configured for determining a blood oxygen level of the user.

18. The apparatus of claim 1, further comprising the external computer-based device programmed for determining at least one anomaly notification in response to at least a portion of the communicated data.

19. The apparatus of claim 1, wherein at least a portion of the communicated data include medical grade data.

20. The apparatus of claim 1, further comprising the data communication module programmed for communicating the processed data to an artificial intelligence module programmed for sleep apnea detection.

21. The apparatus of claim 1, further comprising the data communication module programmed for communicating the processed data to an artificial intelligence module programmed for blood glucose level detection.

22. The apparatus of claim 1, further comprising the data communication module programmed for communicating biometric data comprising one or more of blood oxygen level, blood pressure, heart rate, heart rate variability, resting heart rate, respiratory rate, skin temperature, ambient environment temperature, user activity detection, user steps taken, accelerometer data, sleep stage, and/or sleep apnea data.

23. The apparatus of claim 1, wherein at least a portion of the communicated data comprise data for generating a photoplethysmography (PPG) waveform in connection with determining a blood pressure of the user.

24. The apparatus of claim 1, further comprising the light sensor system programmed for communicating signals indicative of light detected by the photodetectors independent of a skin pigment of a user.

25. The apparatus of claim 1, further comprising the light sensor system programmed for communicating signals indicative of light detected by the photodetectors independent of a skin pigment of a user in response to a combination of:
a predetermined location of at least one of the multiple LEDs on the ring body, and
a predetermined frequency of at least one of the multiple LEDs.

26. The apparatus of claim 1, further comprising the data communication module programmed for communicating biometric data usable by the external computer-based device for determining detection of early stage disease development.

* * * * *